(12) United States Patent
Augeri et al.

(10) Patent No.: US 8,093,245 B2
(45) Date of Patent: Jan. 10, 2012

(54) 4-AMINO-1H-PYRIMIDIN-2-ONE BASED COMPOUNDS, COMPOSITIONS COMPRISING THEM AND METHODS OF THEIR USE

(75) Inventors: David J. Augeri, Princeton, NJ (US); Marianne Carlsen, Yardley, PA (US); Kenneth G. Carson, Princeton, NJ (US); Qinghong Fu, Plainsboro, NJ (US); Alexander Heim-Riether, Newtown, CT (US); Theodore C. Jessop, Lawrenceville, NJ (US); James E. Tarver, Morrisville, PA (US); Jerry A. Taylor, Trenton, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 992 days.

(21) Appl. No.: 11/954,421

(22) Filed: Dec. 12, 2007

(65) Prior Publication Data

US 2008/0182847 A1    Jul. 31, 2008

Related U.S. Application Data

(60) Provisional application No. 60/874,847, filed on Dec. 14, 2006.

(51) Int. Cl.
 C07D 239/47 (2006.01)
 C07D 403/04 (2006.01)
 A61K 31/506 (2006.01)

(52) U.S. Cl. ............... 514/235.8; 514/252.14; 514/274; 544/122; 544/295; 544/296; 544/317

(58) Field of Classification Search .............. 544/122, 544/295, 296, 317; 514/235.8, 252.14, 274
See application file for complete search history.

(56) References Cited

U.S. PATENT DOCUMENTS

| 6,258,825 B1 | 7/2001 | Ozaki |
| 6,653,478 B2 | 11/2003 | Urbanski |
| 2004/0116450 A1 | 6/2004 | Oyama |
| 2005/0245503 A1 | 11/2005 | Cheng |

FOREIGN PATENT DOCUMENTS

| WO | WO 2004007499 | 1/2004 |
| WO | WO 2004069847 | 8/2004 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, pp. 1-7, Aug. 2002.*
Simone, Oncology: Introduction, Cecil Textbook of Medicine, 20th Edition, vol. 1, pp. 1004-1010, 1996.*
Gura et al., Systems for Identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Kaspersen et al., Unconventional Nucleotide Analogues. Part XIV. (2S,4S)-2-Hydroxymethyl- and 2-Carboxy-4-(pyrimidin-1- yl)pyrrolidines, Journal of the Chemical Society, Perkin Transactions 1, 1975, pp. 1798-1802.*
Oh & Hong, Arch. Pham. Med. Chem. 2004, 337, 457-463.
Kaspersen & Pandit, J. Chem. Soc. Perkin Trans. I., 18, 1975, 1798-1802.
International Search Report for Corresponding Patent Application No. PCT/US2007/087331, dated May 13, 2008.

* cited by examiner

*Primary Examiner* — Deepak Rao
(74) *Attorney, Agent, or Firm* — Max Bachrach

(57) ABSTRACT

4-Amino-1H-pyrimidin-2-one-based compounds, compositions comprising them, and methods of their use for the treatment, prevention and management of various diseases and disorders are disclosed. Particular compounds are of formula I:

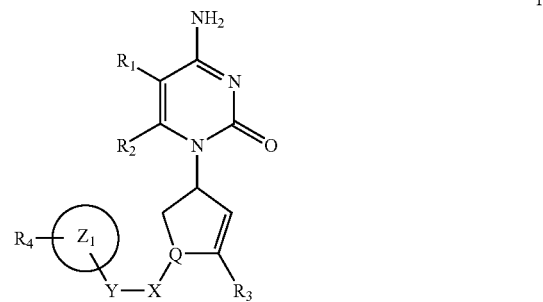

17 Claims, No Drawings

4-AMINO-1H-PYRIMIDIN-2-ONE BASED COMPOUNDS, COMPOSITIONS COMPRISING THEM AND METHODS OF THEIR USE

This application claims priority to U.S. provisional application No. 60/874,847, filed Dec. 14, 2006, the entirety of which is incorporated herein by reference.

1. FIELD OF THE INVENTION

This invention relates to 4-amino-1H-pyrimidin-2-one-based compounds, compositions comprising them, and methods of their use.

2. BACKGROUND

Deoxycytidine kinase is an enzyme involved in deoxynucleoside salvage, supplying precursors for DNA synthesis. Csapó, Z. et al., *Acta Biochimica Polonica* 48(1):251-256, 251 (2001). The enzyme is able to phosphorylate three of the four deoxynucleosides, and also phosphorylates a variety of antineoplastic and antiviral nucleoside analogues. Id.; Chottiner, E. G., et al., *Proc. Natl. Acad. Sci. USA* 88:1531-1535, 1531 (1991). For example, the enzyme reportedly activates cytosineb-D-arabinofuranoside (AraC), fludarabine and cladribine, the chemotherapeutic agents gemcytabine and troxacitabine, and the antivirals 3TC and ddC, which are used in the treatment of HIV infection. Sabini, E. et al, *Nature Stuct. Biol.* 10(7):513-519, 513 (2003).

Although deoxycytidine kinase activates some anti-cancer drugs, reports suggest that at least one anti-cancer drug may act, at least in part, by inhibiting the enzyme. See, e.g., International Application WO04/103374. In this regard, a link between neoplastic transformation and increased deoxycytidine kinase levels in solid cancer tissues has been reported. See Arnér, E. S. J. and Eriksson, S., *Pharmac. Ther.* 67(2): 155-186, 165 (1995). Some deoxycytidine kinase inhibitors have been reported. See, e.g., Krenitsky, T. A. et al., *J. Biol. Chem.* 251(13):4055-4061 (1976); Ward, A. D. and Baker, B. R., *J. Med. Chem.* 20(1):88-92 (1976).

3. SUMMARY OF THE INVENTION

This invention encompasses compounds of the formulae:

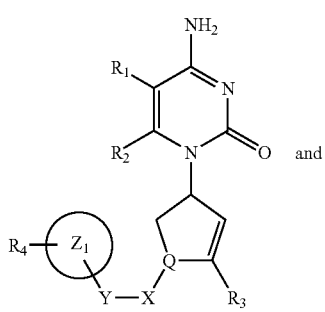

and

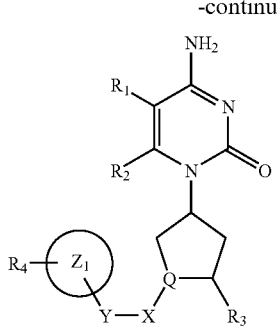

and pharmaceutically acceptable salts and solvates thereof, the various substituents of which are defined herein.

This invention also encompasses methods of treating, managing and preventing diseases and disorders, which comprise administering to a patient in need thereof a therapeutically or prophylactically effective amount of a compound of the invention.

4. DETAILED DESCRIPTION

This invention is directed, in part, to 4-amino-1H-pyrimidin-2-one-based compounds and compositions comprising them. Preferred compounds inhibit deoxycytidine kinase.

4.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$—CH$_3$, and —O(CH$_2$)$_5$CH$_3$. The term "lower alkoxy" refers to —O-(lower alkyl).

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "dCK_IC$_{50}$" means an IC$_{50}$ for human recombinant deoxycytidine kinase as determined using the filter binding assay described in the Examples, below.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "managing cancer," "managing cancer" and "management of cancer" mean reducing the rate of growth of cancerous cells.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "potent deoxycytidine kinase inhibitor" means a compound that has a dCK_IC$_{50}$ of less than about 1 μM.

Unless otherwise indicated, the terms "prevent cancer," "preventing cancer" and "prevention of cancer" mean inhibiting the growth of cancerous cells.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat cancer," "treating cancer" and "treatment of cancer" mean causing apoptosis of cancerous cells.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

4.2. Compounds

This invention is directed, in part, to compounds of formula I:

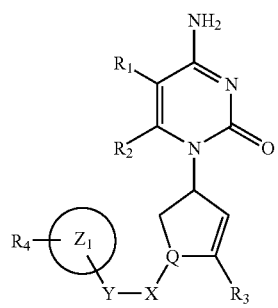

and pharmaceutically acceptable salts and solvates thereof, wherein: Q is C or N; X is a bond, NR$_5$, N(C(O)R$_5$), N(C(O)OR$_5$), O, S, SO$_2$, C, CH, or CH$_2$; Y is a bond, C(O), C(O)NH, C(O)NH$_2$CH$_2$, SO$_2$, NR$_5$, N(C(O)R$_5$), N(C(O)OR$_5$), or CH$_2$, with the proviso that if X and Y are both bonds, they are taken together to form one bond (i.e., one bond connects Q to Z$_1$); Z$_1$ is optionally substituted cycloalkyl, aryl, or heterocycle; R$_1$ is hydrogen, halogen, —OH, —NH$_2$, —NO$_2$, —CN, or optionally substituted alkyl; R$_2$ is hydrogen, halogen, or optionally substituted alkyl; R$_3$ is hydrogen, halogen, —OR$_6$ or —NR$_7$R$_8$; R$_4$ is hydrogen, —C(O)(CH$_2$)$_n$R$_9$, —C(O)NH(CH$_2$)$_n$R$_9$, —NHC(O)(CH$_2$)$_n$R$_9$, or optionally substituted alkyl, aryl, heterocycle, alkyl-aryl, or alkyl-heterocycle; R$_5$ is hydrogen or optionally substituted alkyl, aryl, heterocycle, alkyl-aryl or alkyl-heterocycle; R$_6$ is hydrogen or optionally substituted alkyl, aryl, heterocycle, alkyl-aryl or alkyl-heterocycle; R$_7$ and R$_8$ are each independently hydrogen, or optionally substituted alkyl, aryl, heterocycle, alkyl-aryl or alkyl-heterocycle, or taken together with the nitrogen atom to which they are attached, form an optionally substituted heterocycle; R$_9$ is optionally substituted alkyl, aryl or heterocycle; and n is 0-3.

Certain compounds of formula I are of formula II or III:

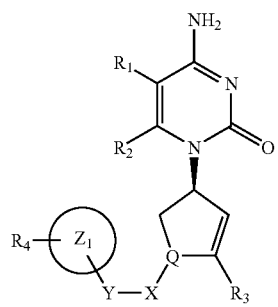

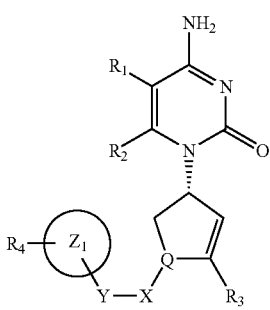

III or diastereomers thereof. For example, certain compounds of formula I are of formula IV or V:

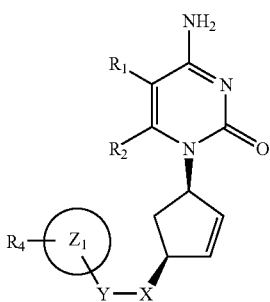

IV

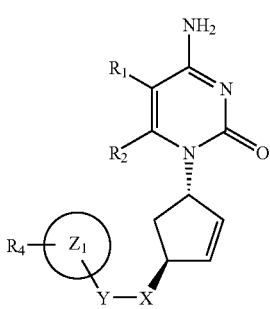

V

Other compounds of formula I are of formula VI or VII:

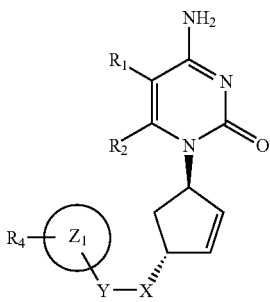

VI

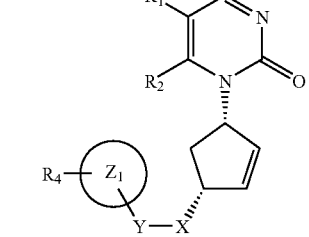

VII

In one embodiment of formulae I-VIII, $Z_1$ is not substituted with anything other than $R_4$. In another embodiment, $Z_1$ is optionally substituted with at least one halogen. In another embodiment, $Z_1$ is optionally substituted aryl. In another embodiment, $Z_1$ is heteroaryl (e.g., pyridine, pyridazine, pyrimidine, pyrazine, quinoline, quinoxaline, quinazoline). In another embodiment, $Z_1$ is a multi-ring aryl moiety (e.g., biphenyl). In another embodiment, $Z_1$ is a substituted heteroaryl.

In another embodiment of formulae I-VIII, Q is N.

In another embodiment of formulae I-VII, X is a bond. In another embodiment, X is $NR_5$ or $SO_2$. In another embodiment, X is $NR_5$ and $R_5$ is hydrogen or methyl. In another embodiment, X is O or $CH_2$.

In another embodiment of formulae I-VII, Y is a bond (e.g., a single bond). In another embodiment, Y is $SO_2$ or C(O). In another embodiment, Y is $NR_5C(O)$. In another embodiment of formulae I-VII, X and Y together form a single bond. In another embodiment, X is a bond and Y is NHC(O).

In another embodiment of formulae I-VII, $R_1$ is hydrogen or halogen (e.g., fluoro). In another embodiment, $R_1$ is optionally substituted alkyl.

In another embodiment of formulae I-VII, $R_2$ is hydrogen. In another embodiment, $R_2$ is halogen.

In another embodiment of formulae I-VII, $R_3$ is hydrogen. In another embodiment, $R_3$ is —$OR_6$.

In another embodiment of formulae I-VII, $R_4$ is hydrogen. In another embodiment, $R_4$ is —$C(O)(CH_2)_nR_9$ and n is 0 or 1. In another embodiment, $R_4$ is —$C(O)NH(CH_2)_nR_9$ and n is 0 or 1. In another embodiment, $R_4$ is —$NHC(O)(CH_2)_nR_9$ and n is 0 or 1. In another embodiment, $R_4$ is optionally a substituted heteroaryl. In another embodiment, $R_4$ is a optionally substituted bicyclic heteroaryl (e.g., quinoline, quinoxaline, quinazoline, 1,7-naphthyridine, benzofuran, benzo[b]thiophene, thieno[2,3-b]pyridine, thieno[2,3-c]pyridine, indole, isoindole, pyrrolo[3,4-c]pyridine).

In another embodiment of formulae I-VII, $R_5$ is hydrogen. In another embodiment, $R_5$ is optionally substituted alkyl. In another embodiment, $R_5$ is optionally substituted aryl.

In another embodiment of formulae I-VII, $R_6$ is hydrogen. In another embodiment, $R_6$ is optionally substituted alkyl.

In another embodiment of formulae I-VII, $R_7$ and $R_8$ are each independently hydrogen or optionally substituted alkyl. In another embodiment, $R_7$ and $R_8$ are both hydrogen. In another embodiment, $R_7$ and $R_8$ are taken together with the nitrogen atom to which they are attached to form an optionally substituted heterocycle.

In another embodiment of formulae I-VII, $R_9$ is not substituted. In another embodiment, $R_9$ is $CH_3$, $CH(CH_3)_2$, $C(CH_3)_3$, or a halogenated derivative thereof. In another embodiment, $R_9$ is optionally substituted cycloalkyl. In another embodiment, $R_9$ is an optionally substituted aryl. In another embodiment, $R_9$ is an optionally substituted non-aromatic heterocycle. In another embodiment, $R_9$ is an optionally substituted heteroaryl.

In another embodiment of formulae I-VII, n is 0. In another embodiment, n is 1. In another embodiment, n is 2. In another embodiment, n is 3.

The invention also encompasses compounds of formula VIII:

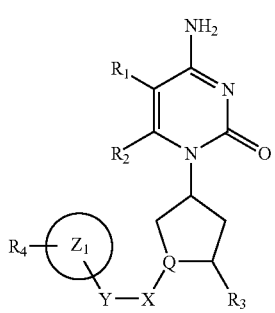

VIII and pharmaceutically acceptable salts and solvates thereof, wherein: Q is C or N; X is a bond, $NR_5$, $N(C(O)R_5)$, $N(C(O)OR_5)$, O, S, $SO_2$, C, CH, or $CH_2$; Y is a bond, C(O), C(O)NH, $C(O)NH_2CH_2$, $SO_2$, $NR_5$, $N(C(O)R_5)$, $N(C(O)OR_5)$, or $CH_2$, with the proviso that if X and Y are both bonds, they are taken together to form one bond (i.e., one bond connects Q to $Z_1$); $Z_1$ is optionally substituted cycloalkyl, aryl, or heterocycle; $R_1$ is hydrogen, halogen, —OH, —$NH_2$, —$NO_2$, —CN, or optionally substituted alkyl; $R_2$ is hydrogen, halogen, or optionally substituted alkyl; $R_3$ is hydrogen, halogen, —$OR_6$ or —$NR_7R_8$; $R_4$ is hydrogen, —$C(O)(CH_2)_nR_9$, —C(O)NH$(CH_2)_nR_9$, —NHC(O)$(CH_2)_nR_9$, or optionally substituted alkyl, aryl, heterocycle, alkyl-aryl, or alkyl-heterocycle; $R_5$ is hydrogen or optionally substituted alkyl, aryl, heterocycle, alkyl-aryl or alkyl-heterocycle; $R_6$ is hydrogen or optionally substituted alkyl, aryl, heterocycle, alkyl-aryl or alkyl-heterocycle; $R_7$ and $R_8$ are each independently hydrogen, or optionally substituted alkyl, aryl, heterocycle, alkyl-aryl or alkyl-heterocycle, or taken together with the nitrogen atom to which they are attached, form an optionally substituted heterocycle; $R_9$ is optionally substituted alkyl, aryl or heterocycle; and n is 0-3.

In one embodiment, $Z_1$ and $R_4$ taken together are not 4-methylphenyl if Q is N and X and Y taken together are $SO_2$ (i.e., X is a bond and Y is $SO_2$, or X is $SO_2$ and Y is a bond). In a specific embodiment, $Z_1$ and $R_4$ taken together are not 4-methylphenyl when Q is N, X and Y taken together are $SO_2$, and $R_3$ is —$CH_2CH_2OH$.

Certain compounds of formula VIII are of formula IX or X:

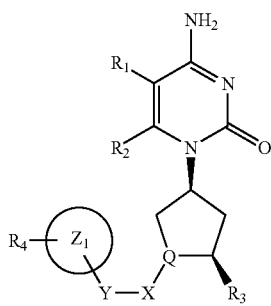

IX

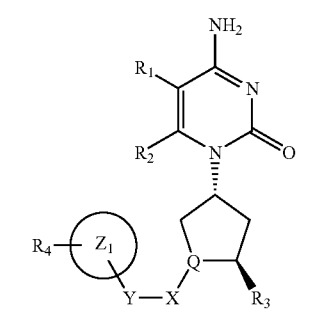

X or diastereomers thereof. For example, certain compounds of formula VIII are of formula XI or XII:

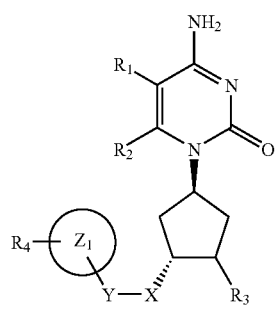

XI

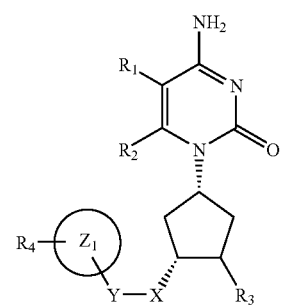

XII

Other compounds are of formula XIII or XIV:

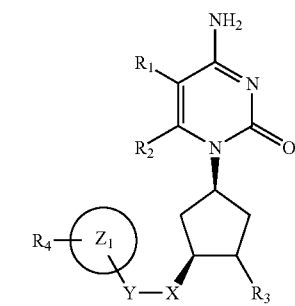

XIII

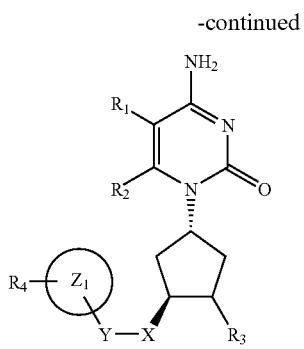

In one embodiment of formulae VIII-XIV, $Z_1$ is not substituted with anything other than $R_4$. In another embodiment, $Z_1$ is optionally substituted with at least one halogen. In another embodiment, $Z_1$ is optionally substituted aryl. In another embodiment, $Z_1$ is heteroaryl (e.g., pyridine, pyridazine, pyrimidine, pyrazine). In another embodiment, $Z_1$ is a multi-ring aryl moiety (e.g., biphenyl). In another embodiment, $Z_1$ is a substituted heteroaryl.

In another embodiment of formulae VIII-XIV, Q is N.

In another embodiment of formulae VIII-XIV, X is a bond. In another embodiment, X is $NR_5$ or $SO_2$. In another embodiment, X is $NR_5$ and $R_5$ is hydrogen or methyl. In another embodiment, X is O or $CH_2$.

In another embodiment of formulae VIII-XIV, Y is a bond (e.g., a single bond). In another embodiment, Y is $SO_2$ or C(O). In another embodiment, Y is $NR_5C(O)$. In another embodiment of formulae VIII-XIV, X and Y together form a single bond.

In another embodiment, X is a bond and Y is NHC(O).

In another embodiment of formulae VIII-XIV, $R_1$ is hydrogen or halogen (e.g., fluoro). In another embodiment, $R_1$ is optionally substituted alkyl.

In another embodiment of formulae VIII-XIV, $R_2$ is hydrogen. In another embodiment, $R_2$ is halogen.

In another embodiment of formulae VIII-XIV, $R_3$ is hydrogen. In another embodiment, $R_3$ is —$OR_6$.

In another embodiment of formulae VIII-XIV, $R_4$ is hydrogen. In another embodiment, $R_4$ is —$C(O)(CH_2)_nR_9$ and n is 0 or 1. In another embodiment, $R_4$ is —$C(O)NH(CH_2)_nR_9$ and n is 0 or 1. In another embodiment, $R_4$ is —$NHC(O)(CH_2)_nR_9$ and n is 0 or 1. In another embodiment, $R_4$ is optionally a substituted heteroaryl. In another embodiment, $R_4$ is a optionally substituted bicyclic heteroaryl (e.g., quinoline, 1,7-naphthyridine, benzofuran, benzo[b]thiophene, thieno[2,3-b]pyridine, thieno[2,3-c]pyridine, indole, isoindole, pyrrolo[3,4-c]pyridine).

In another embodiment of formulae VIII-XIV, $R_5$ is hydrogen. In another embodiment, $R_5$ is optionally substituted alkyl. In another embodiment, $R_5$ is optionally substituted aryl.

In another embodiment of formulae VIII-XIV, $R_6$ is hydrogen. In another embodiment, $R_6$ is optionally substituted alkyl.

In another embodiment of formulae VIII-XIV, $R_7$ and $R_8$ are each independently hydrogen or optionally substituted alkyl. In another embodiment, $R_7$ and $R_8$ are both hydrogen. In another embodiment, $R_7$ and $R_8$ are taken together with the nitrogen atom to which they are attached to form an optionally substituted heterocycle.

In another embodiment of formulae VIII-XIV, $R_9$ is not substituted. In another embodiment, $R_9$ is $CH_3$, $CH(CH_3)_2$, $C(CH_3)_3$, or a halogenated derivative thereof. In another embodiment, $R_9$ is optionally substituted cycloalkyl. In another embodiment, $R_9$ is an optionally substituted aryl. In another embodiment, $R_9$ is an optionally substituted non-aromatic heterocycle. In another embodiment, $R_9$ is an optionally substituted heteroaryl.

In another embodiment of formulae VIII-XIV, n is 0. In another embodiment, n is 1.

In another embodiment, n is 2. In another embodiment, n is 3.

Compounds of the invention contain one or more stereocenters, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, NY, 1962); and Wilen, S. H., *Tables of Resolving Agents and Optical Resolutions*, p. 268 (E. L. Eliel, Ed., Univ. of Notre Dame Press, Notre Dame, IN, 1972).

This invention further encompasses stereoisomeric mixtures of compounds disclosed herein. It also encompasses configurational isomers of compounds disclosed herein, either in admixture or in pure or substantially pure form, such as cis (Z) and trans (E) alkene isomers.

Preferred compounds are potent deoxycytidine kinase inhibitors. For example, particular compounds have a $dCK\_IC_{50}$ of less than about 1000, 500, 250, 100, 50, 10, 5, 2.5 or 1 nM.

Particular compounds inhibit thymidine kinase with an $IC_{50}$ of greater than about 1, 2.5, 5 or 10 µM, as determined using the assay described in the Examples below.

Particular compounds inhibit uridine kinase with an $IC_{50}$ of greater than about 1, 2.5, 5 or 10 µM, as determined using the assay described in the Examples below.

4.3. Methods of Synthesis

Compounds of the invention (i.e., compounds disclosed herein) can be prepared by methods known in the art, as well as the methods described herein. For example, cyclopentaneol cytosine derivatives can be synthesized from cis-4-acetoxycyclopent-2-enol as shown below in Scheme 1:

Scheme 1

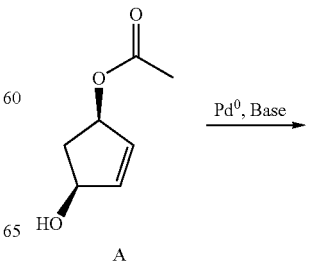

A

-continued

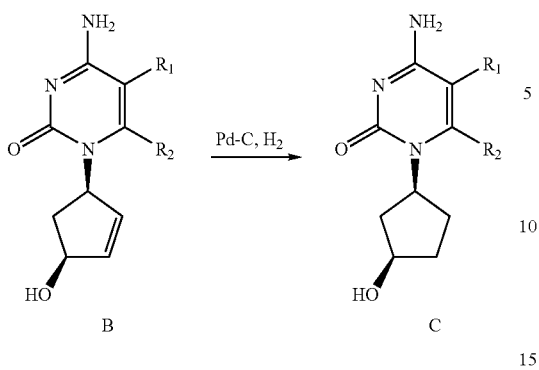

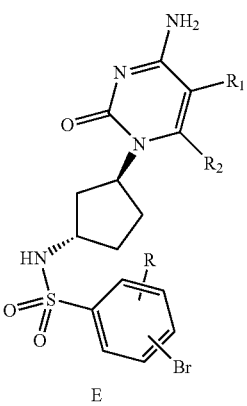

The subsequent alcohols can either be reduced and treated with a Mitsonobu inversion protocol, or directly treated with the Mitosonobu protocol to give access to both cis- and trans-substituted cyclopentanes. Selected compounds and intermediates can be prepared from carbamate-protected sulfonamides or imides employing a Mitsonobu inversion reaction on an intermediate alcohol. The subsequent carbamates and imides can be cleaved to yield both target compounds and late stage bromide E intermediates, as shown below in Scheme 2:

In this generic scheme, R refers to any suitable moiety and can be a portion or precursor of $Z_1$ or $R_4$. Moreover, it should be understood that if moieties in the final product, such as $R_1$ and $R_2$, are reactive, they may be protected (and subsequently deprotected) using methods known in the art, if necessary.

The amine intermediate G can be prepared as shown below in Scheme 3:

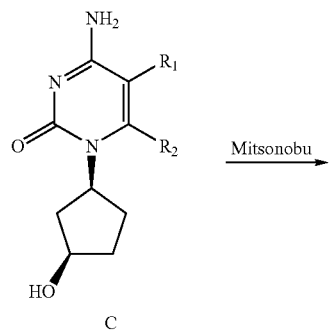

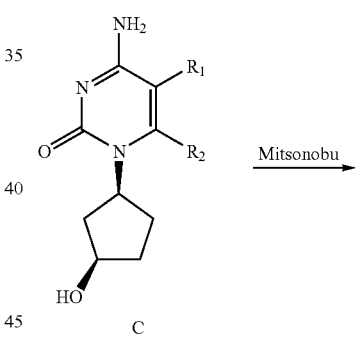

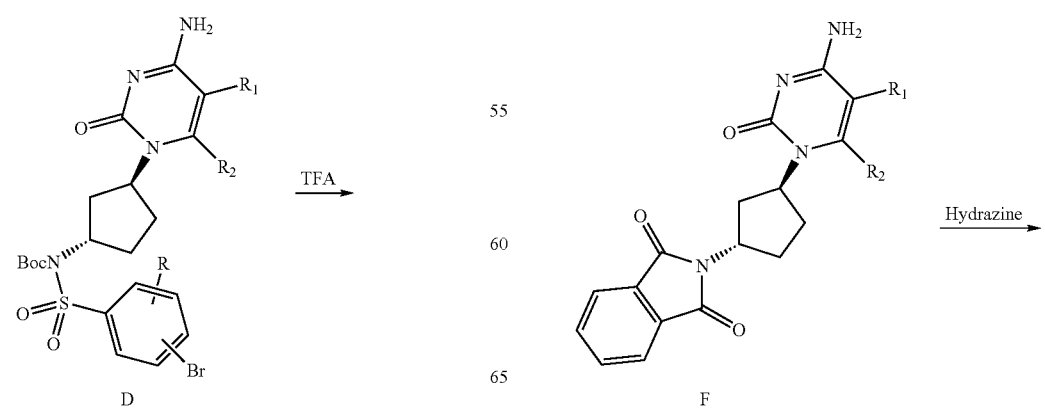

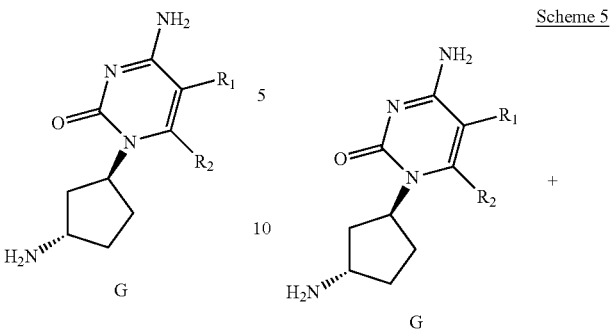
Intermediate G can also be prepared as shown in Scheme 4:
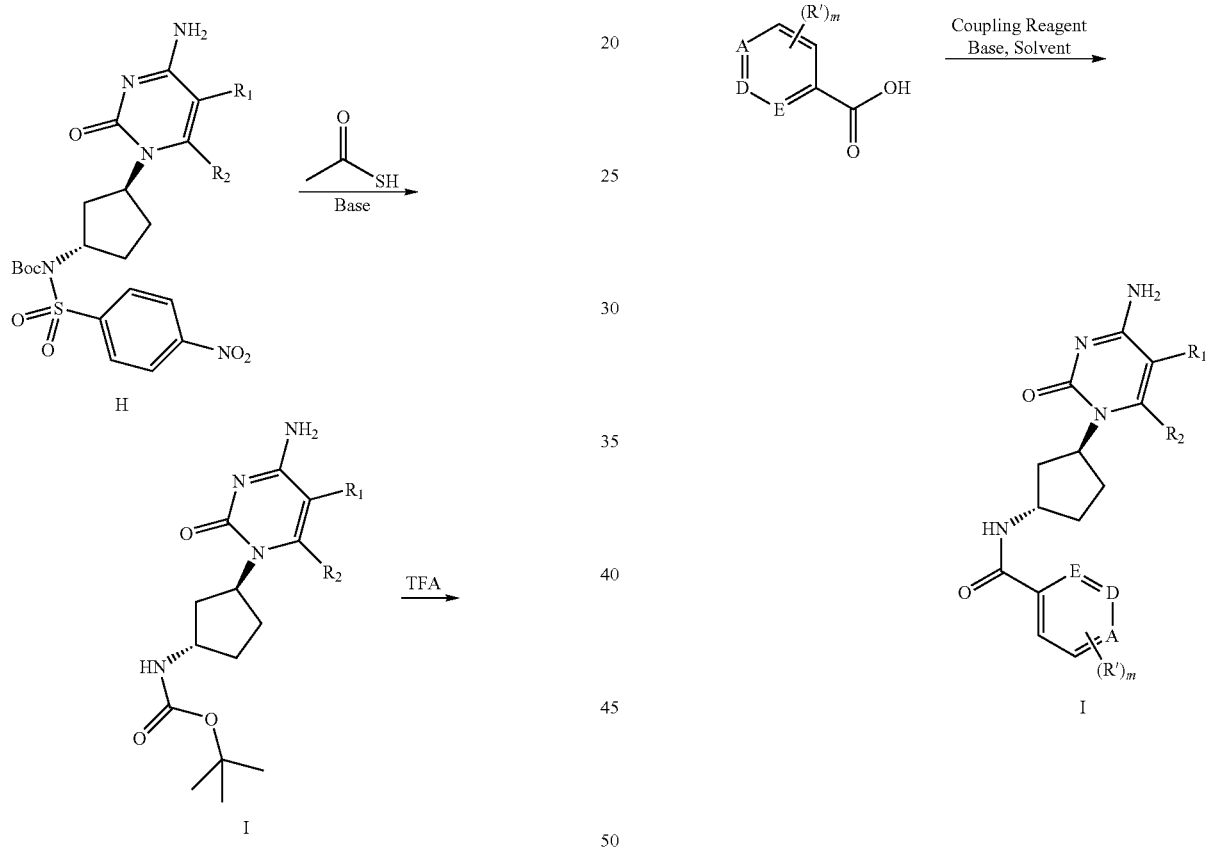
Intermediate amine G can be coupled with carboxylic acids or acid chlorides, which are commercially available or readily made, to obtain final and near-final products, as shown below in Schemes 5 and 6:
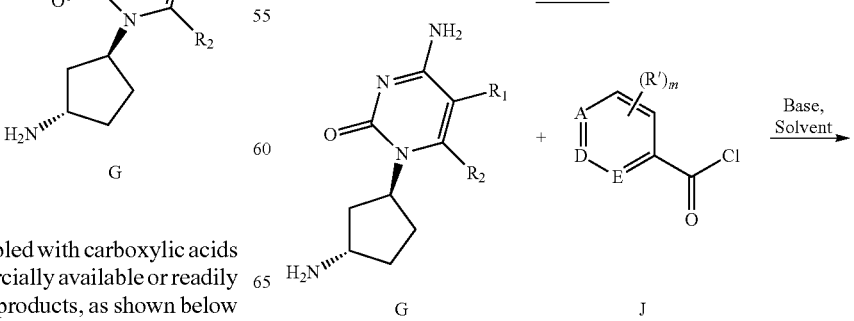

-continued

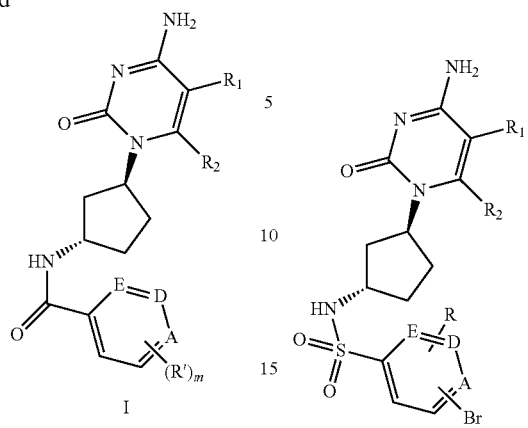

I

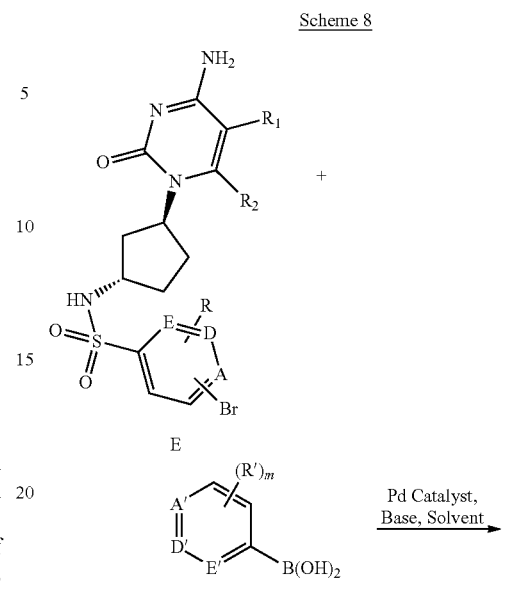

In these generic schemes, A, D and E refer to carbon or a heteroatom, R' refers to any suitable moiety and can be a portion or precursor of $Z_1$ or $R_4$, and m is an integer (e.g., 1-3). For example, when R' is a carboxylic acid, compounds of formula I can be coupled with commercially available amines to afford amides, as shown in Scheme 7:

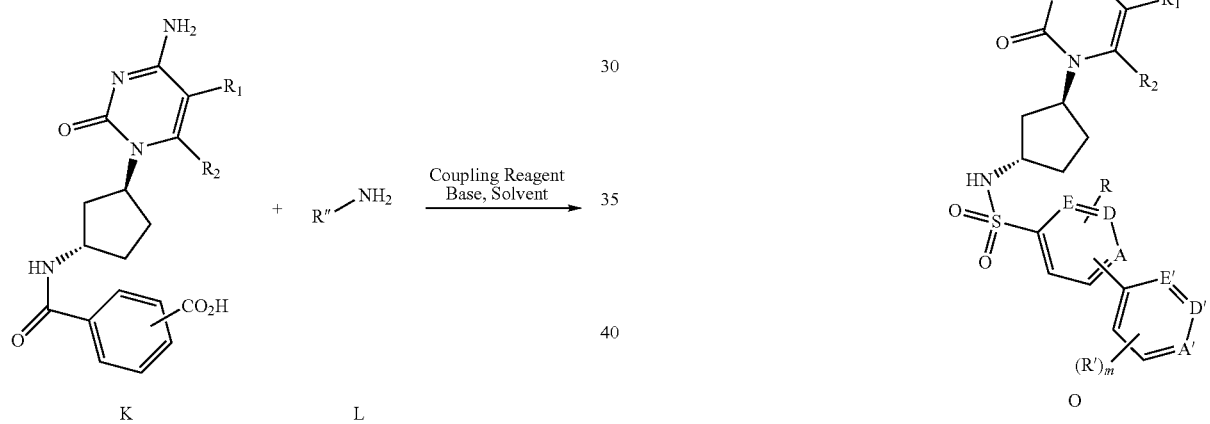

Final and near-final products can also be prepared by coupling late stage intermediate aryl bromides, such as those of formula E, with aryl and heterocyclic boronic acids and boronic esters using Suzuki coupling reaction conditions. An example of this is shown below in Schemes 8:

Similarly, aryl bromides of formula Q can be reacted with commercially available aryl and heterocyclic boronic acids and boronic esters using Suzuki coupling reaction conditions, as shown in Scheme 9:

Scheme 9

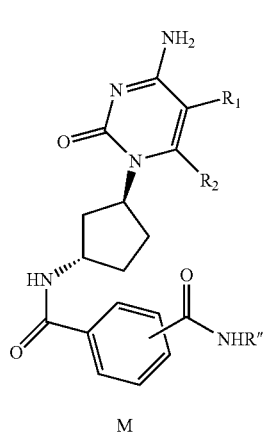

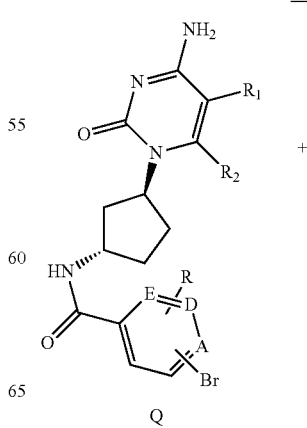

Q

-continued

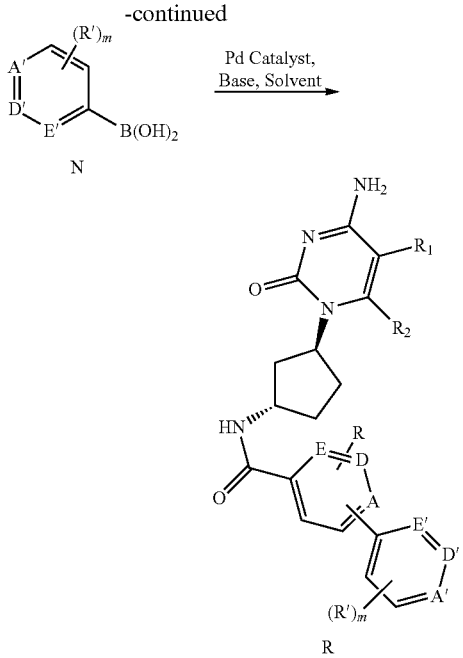

The general approaches shown above are readily modified to obtain a wide variety of compounds encompassed by the invention. For example, intermediate B can be treated with Boc-sulfonamides or phthalimide under Mitsonobu conditions to generate cyclopentene compounds similar to general structures D and F, and also allow for compounds with syn stereochemistry. These compounds can then be treated under deprotection conditions (e.g., trifluoroacetic acid, hydrazine) to yield target cyclopentene compounds and intermediates similar to structures E and G, respectively. The subsequent cyclopentene G intermediates can be acylated using techniques in the art, such as those shown above in Schemes 5 and 6. Similarly, cyclopentene structures analogous to E can be coupled with aryl derivatives using known techniques, such as those shown above in Schemes 8 and 9.

4.4. Methods of Use

This invention encompasses a method of reducing (e.g., inhibiting) the activity of deoxycytidine kinase, which comprises contacting deoxycytidine kinase with a compound of the invention (i.e., a compound disclosed herein). In one embodiment, the deoxycytidine kinase is in vitro. In another, the deoxycytidine kinase is in vivo.

Also encompassed is a method of treating, managing or preventing cancer in a patient, which comprises inhibiting deoxycytidine kinase activity in the patient. A particular patient is undergoing chemotherapy.

One embodiment of the invention encompasses a method of treating, managing or preventing cancer in a patient, which comprises administering to the patient a therapeutically or prophylactically effective amount of a potent deoxycytidine kinase inhibitor. Particular potent deoxycytidine kinase inhibitors are disclosed herein. In one method, the potent deoxycytidine kinase inhibitor is administered adjunctively with another chemotherapeutic agent (e.g., cyclophosphamide (CTX) or a combination comprising it, such as CHOP).

Cancers include solid cancers (e.g., colon carcinomas, brain tumors, head and neck tumors, malignant melanomas and soft tissue sarcomas), leukemia, and lymphoma.

Another embodiment of the invention encompasses a method of improving the effectiveness of a chemotherapeutic agent in a patient undergoing chemotherapy with the chemotherapeutic agent, which comprises inhibiting deoxycytidine kinase activity in the patient. Examples of chemotherapeutic agents include CTX.

In each of these various methods, the amount, route of administration and dosing schedule of a compound will depend upon factors such as the specific indication to be treated, prevented, or managed, and the age, sex and condition of the patient. The roles played by such factors are well known in the art, suitable doses and dosing regimens can be determined by the skilled artisan.

4.5. Pharmaceutical Compositions

This invention encompasses pharmaceutical compositions and dosage forms comprising compounds of the invention as their active ingredients. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

5. EXAMPLES

Aspects of this invention may be understood from the following examples.

5.1. Preparation of N-[3-(4-amino-5-fluoro-2-oxo-2H-pyrimidin-1-yl)-cyclopentyl]-3-bromo-benzenesulfonamide The captioned compound was prepared according to Scheme 10, which provides an example of what is referred to herein as General Method A:

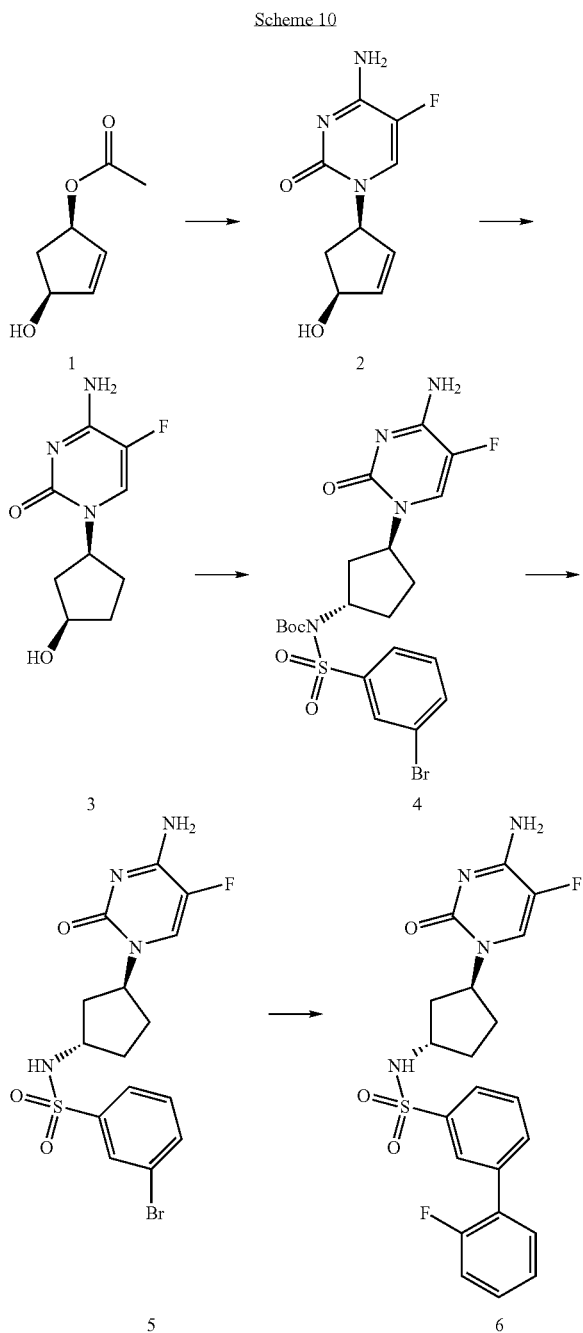

Scheme 10

Synthesis of 2: To a mixture of (1S,4R)-cis-4-acetoxy-2-cyclopenten-1-ol (10.8 g, 76.0 mmol) dipalladium-tris-dibenzylideneacetone (1.70 g, 1.90 mmol) and triphenylphosphine (1.00 g, 3.8 mmol) was added anhydrous tetrahydrofuran (100 mL). The slurry was degassed with nitrogen at room temperature for about 15 minutes. In a 1 L 3-neck round bottomed flask equipped with reflux condenser, a mixture of 5-fluorocytosine (9.80 g, 76.0 mmol) and triphenylphosphine (1.00 g, 3.8 mmol) was suspended in anhydrous dimethylformamide (200 mL). The vigorously stirred slurry of 5-F-cytosine was heated to 60° C. and treated with sodium t-butoxide (7.20 g, 75.0 mmol), which afforded a white precipitate. The resulting thick slurry of anion was treated with the solution of acetate/catalyst via cannula over 10 minutes. The resulting dark green heterogeneous mixture was stirred under nitrogen at 70° C. for 12 hours, and the solvent was removed in vacuo. The residue was dry-loaded onto 400 g silica gel. Silica gel plug filtration (6×10 cm $SiO_2$) followed by trituration with acetonitrile/ethyl acetate afforded the title compound as an off-white solid (12.65 g, 80%). A similar procedure was used with cytosine as the nucleophile.

Synthesis of 3: To a suspension 10% palladium on carbon (Degussa, 0.6 g) in HPLC methanol was added 4-amino-5-fluoro-1-(4-hydroxy-cyclopent-2-enyl)-1H-pyrimidin-2-one (2) (3.2 g, 14.6 mmol). The reaction was evacuated thrice and left under $H_2$ (1 atm) for 12 hours. After completion, the reaction was filtered through celite and the filtrate was concentrated to a white solid. The solid was dissolved in hot water and frozen and concentrated on a lyophilizer to dryness to recover 4-amino-5-fluoro-1-(3-hydroxy-cyclopentyl)-1H-pyrimidin-2-one (3) as a fluffy white solid (3.1 g), which was used without further purification.

Synthesis of 4: To a suspension of alcohol 3 (2.0 g, 9.48 mmol), N-Boc-sulfonamide (4.5 g, 13.3 mmol), and triphenylphospine (3.7 g, 14.2 mmol) in tetrahydrofuran (158 mL) was added diethyl azodicarboxylate (DEAD) (2.2 mL, 14.2 mmol) dropwise via syringe. Upon addition, the reaction became clear yellow solution, and the reaction was followed by HPLC. After 16 hours, silica was added and the reaction was concentrated/adhered onto silica. The silica pad was loaded onto a column and purified by column chromatography (5% MeOH—$CH_2Cl_2$) to provide 4 as a light tan foam.

Synthesis of 5: The Boc-sulfonamide 4 was dissolved in dichloromethane (180 mL). Trifluoroacetic acid (100 mL) was added and the reaction was stirred 18 hours. The reaction was concentrated and azeotroped with toluene to remove excess TFA. The crude orange residue was dissolved in dichloromethane and then purification by column chromatography (5% MeOH—$CH_2Cl_2$-10% MeOH—$CH_2Cl_2$) gave 2.9 g (71% over 3 steps) of the N-[3-(4-amino-5-fluoro-2-oxo-2H-pyrimidin-1-yl)-cyclopentyl]-3-bromo-benzenesulfonamide (5).

Synthesis of 6: To a solution of N-[3-(4-amino-5-fluoro-2-oxo-2H-pyrimidin-1-yl)-cyclopentyl]-3-bromo-benzenesulfonamide (66 mg, 0.153 mmol) in acetonitrile (2.5 mL), 2-fluorophenylboronic acid (35 mg, 0.25 mmol), [1,1'-bis(diphenylphosphino) ferrocene]dichloropalladium (20 mg, 0.024 mmol) and 2M $Na_2CO_3$ solution (2.5 mL) were added, the mixture was stirred for 30 seconds. The reaction was completed by microwave at 120° C. for ten minutes. The organic phase of the reaction mixture was filtered and purified by a reverse phase preparative HPLC, giving 26 mg (38%) 2'-fluoro-biphenyl-3-sulfonic acid [3-(4-Amino-5-fluoro-2-oxo-2H-pyrimidin-1-yl)-cyclopentyl]-amide (6) as a white solid.

5.2. Preparation of N-[3-(4-Amino-5-fluoro-2-oxo-2H-pyrimidin-1-yl)-cyclopentyl]-3-bromo-benzamide The captioned compound was prepared according to Scheme 11, which provides an example of what is referred to herein as General Method B:

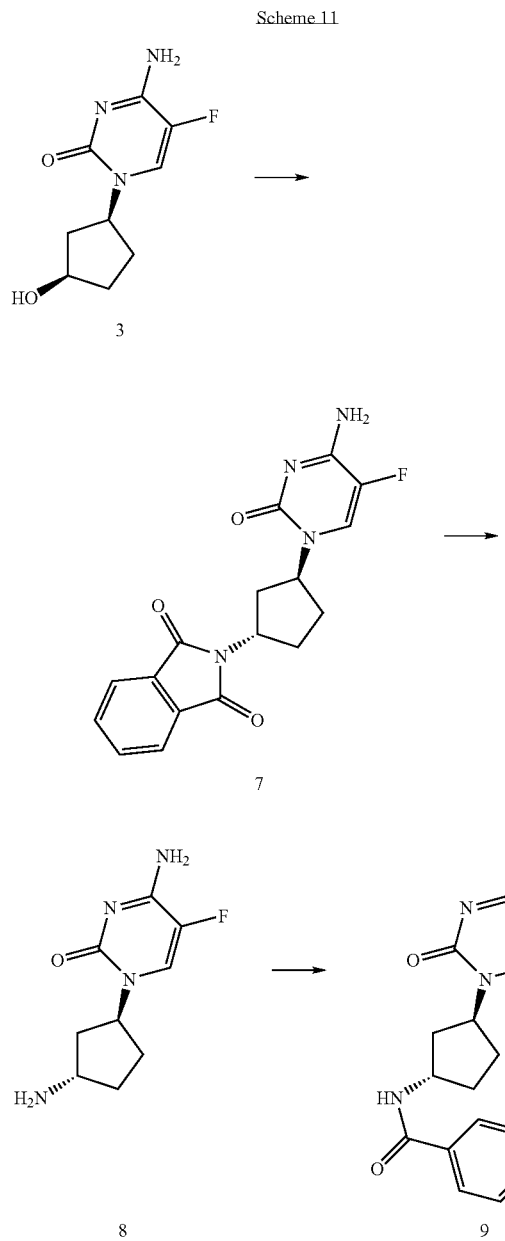

Synthesis of 7: To a suspension of alcohol 3 (2.0 g, 9.39 mmol) in tetrahydrofuran (30 mL) was added phthalimide (2.70 g, 18.8 mmol) and triphenylphosphine (4.93 g, 18.8 mmol). To the suspension was added DEAD (2.9 mL, 18.8 mmol), which caused the reaction mixture to become a clear yellow solution. The reaction was allowed to stir for 24 hours at room temperature, and was concentrated in vacuo to give an orange oil. The crude mixture was dissolved in ethanol (20 mL) and concentrated HCl (6 mL) was added. This mixture was stirred at room temperature for 24 hours and concentrated in vacuo to give an orange oil. The crude material was purified by flash chromatography (SiO$_2$; 5% MeOH—CH$_2$Cl$_2$ with 0.25% NH$_4$OH) to give 3.0 g (93%) of phthalimide 7.

Synthesis of 8: To a solution of phthalimide 7 (0.21 g, 0.61 mmol) in ethanol (5 mL) was added hydrazine (0.2 mL, excess). The solution was heated to reflux for 1 hour and then concentrated in vacuo. The amine (8) as crude material was used without further purification.

Synthesis of 9: To a suspension of 3-bromobenzoic acid (0.38 g, 1.89 mmol) in DMF (1 mL) was added HATU (0.718 mg, 1.89 mmol) and N-methylmorpholine (309 uL, 1.89 mmol), which caused the suspension to become a clear yellow solution. After 10 minutes of stirring, the crude amine 8 was added as a solution in DMF (4 mL) to the reaction mixture. The mixture was stirred at room temperature for 24 hours and then concentrated in vacuo to give a brown solid. The crude material was purified by reversed phase preparative HPLC to give 150 mg (40%) of N-[3-(4-amino-5-fluoro-2-oxo-2H-pyrimidin-1-yl)-cyclopentyl]-3-bromo-benzamide (9).

5.3. Preparation of N-[3-(4-Amino-5-fluoro-2-oxo-2H-pyrimidin-1-yl)-cyclopentyl]-3-bromo-benzamide The captioned compound was prepared according to Scheme 12, which provides an example of what is referred to herein as General Method C:

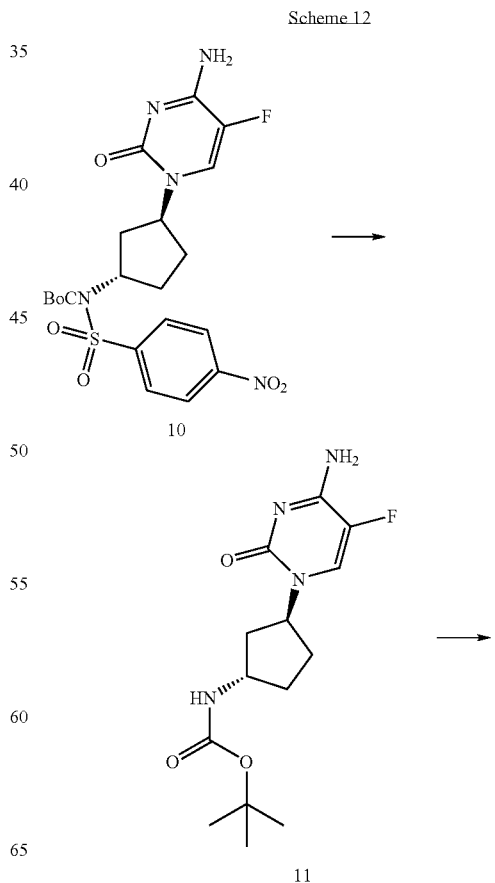

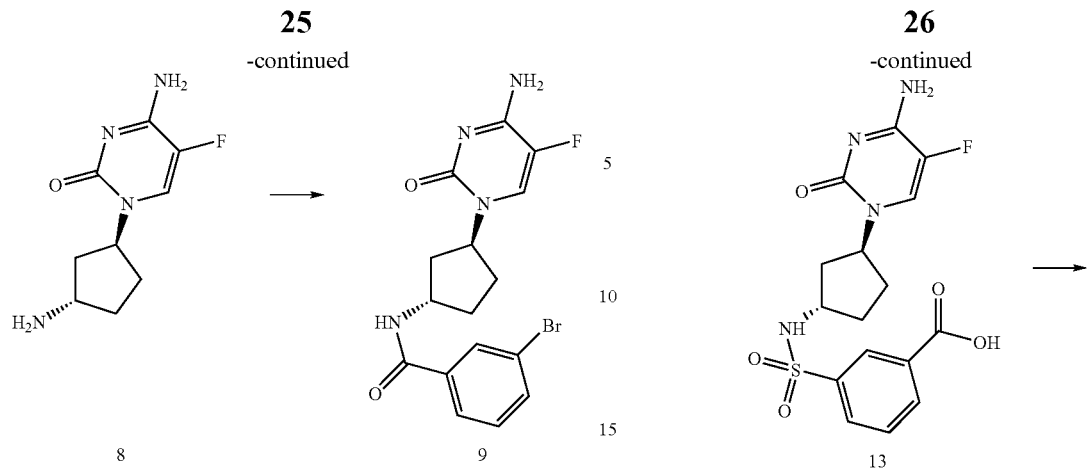

The Boc-sulfonamide intermediate 10 was synthesized using General Method A.

Synthesis of 11: Compound 10 was dissolved in acetonitrile (200 mL) and then treated with thiophenol (2.15 mL, 21.0 mmol) and potassium carbonate (7.245 g, 52.5 mmol). After 2 hours, the starting material had been consumed (as determined by HPLC or LC/MS with UV detection at 290 nm). The crude reaction mixture was poured onto a column of silica gel (4"×6") and purified by column chromatography, eluting with acetonitrile to 4:1 acetonitrile/methanol. Appropriate fractions were collected and the solvent removed in vacuo to afford 3.1 g (51% over 2 steps) of 11.

Synthesis of 8: To a suspension of 11 (2.8 g) in 1,4-dioxane (40 mL) was added HCl (15 ml of a 4M solution in 1,4-dioxane). After 3 hours, the solvent was removed in vacuo to afford the HCl salt of 8 (2.5 g, quantitative yield) as a white solid.

Synthesis of 9: The HCl salt of 8 generated above (630 mg) was stirred in acetonitrile (20 mL) and saturated sodium bicarbonate (5 mL). The solution was cooled at −15° C. and a solution of 3-bromobenzoylchloride (436 mg) in acetonitrile (5 mL) was added dropwise. The reaction was allowed to warm to room temperature overnight. The organic layer was removed, dried over sodium sulfate and evaporated to give 9 (824 mg, 95% yield) as a white solid.

5.4. Preparation of 3-[3-(Amino-5-fluoro-2-oxo-2H-Pyrimidin-1-yl)-cyclopentylsulfamoyl]-N-phenyl-benzamide The captioned compound was prepared according to Scheme 13, which provides an example of what is referred to herein as General Method D:

Scheme 13

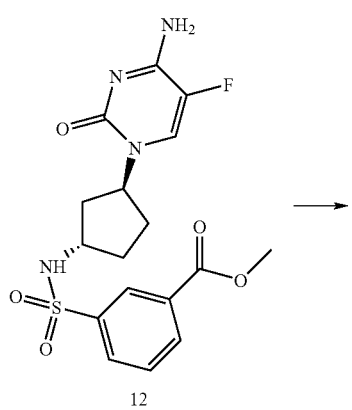

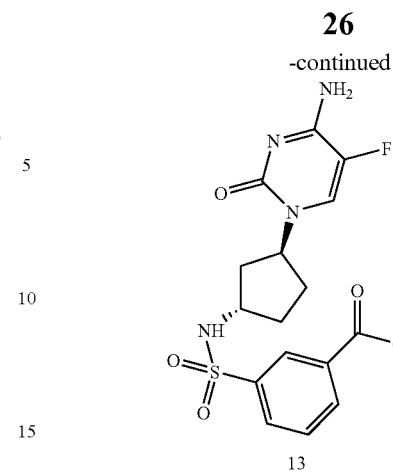

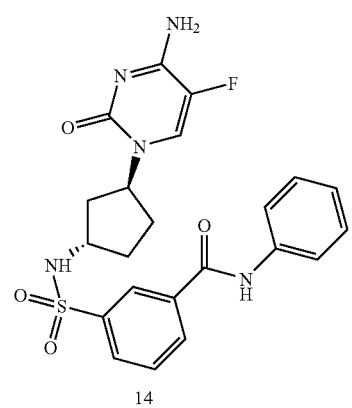

The methyl ester intermediate 12 was synthesized using general method A.

Synthesis of 13: To a solution of methyl ester (0.82 g, 2.0 mmol) in tetrahydrofuran (10 mL) was added 1N NaOH solution (10 mL) at room temperature and then heated to 5° C. for 2 hours. The reaction was cooled, then the solution was acidified to pH 5-6 with 2N HCl solution, and was cooled in the refrigerator for 10 minutes. The precipitate was filtered and collected, washed with small amount of water and dried to give the acid 13 (0.48 g, 60%).

Synthesis of 14: Acid 13 (0.10 g, 0.25 mmol) was suspended in tetrahydrofuran (10 mL) in a 40 mL vial with a magnetic stirring. Amine (0.093 g, 1.0 mmol) was added, followed by HATU (0.19 g, 0.50 mmol). The vial was capped and put in shaker at 50° C. overnight. After cooled to room temperature, the solution was transferred to round bottom flask and removed solvent. The residue was purified with preparative HPLC and dried via lyophylization to give 3-[3-(amino-5-fluoro-2-oxo-2H-pyrimidin-1-yl)-cyclopentylsulfamoyl]-N-phenyl-benzamide (14) as a white solid.

5.5. Preparation of N-[3-(4-Amino-5-fluoro-2-oxo-2H-pyrimidin-1-yl)-cyclopentyl]-3-cyclohexyl-benzenesulfonamide The captioned compound was prepared according to Scheme 14, which provides an example of what is referred to herein as General Method E:

Scheme 14

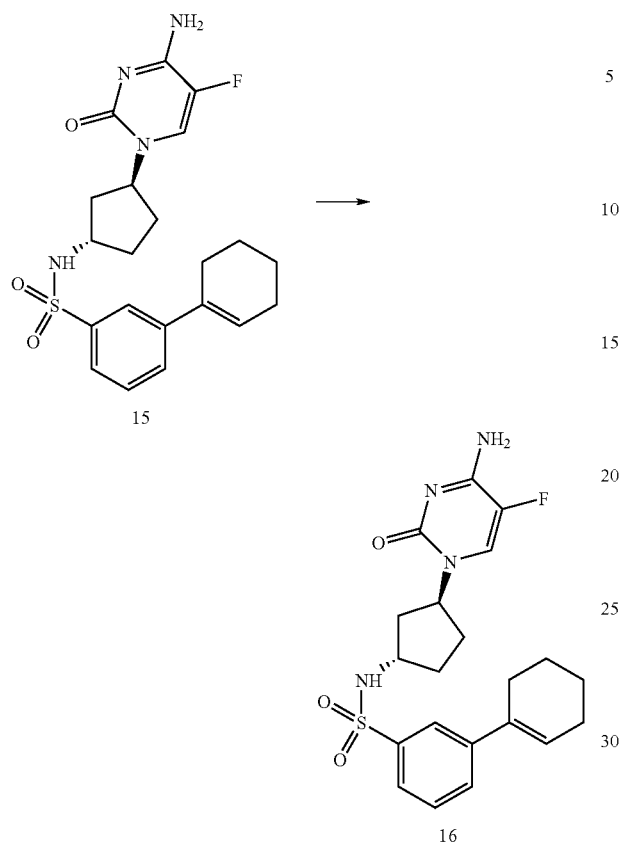

The cyclohexene intermediate 15 was synthesized by general method A. The cyclohexene (20 mg, 0.046 mmol) was dissolved in methanol (10 mL). After degassing with vacuum, the solution was treated with $H_2$ (1 atmosphere) with 10% Pd on carbon (0.010 g) for 2 hours. The catalyst was then filtered and solvent was removed in vacuo to give N-[3-(4-amino-5-fluoro-2-oxo-2H-pyrimidin-1-yl)-cyclopentyl]-3-cyclohexyl-benzenesulfonamide 16 as a white solid (18 mg, 88%).

5.6. Preparation of N-((1S,3S)-3-(4-amino-5-fluoro-2-oxo-2H-pyrimidin-1-yl)cyclopentyl)-4-benzylbenzenesulfonamide The captioned compound was prepared according to Scheme 15, which provides an example of what is referred to herein as General Method F:

Scheme 15

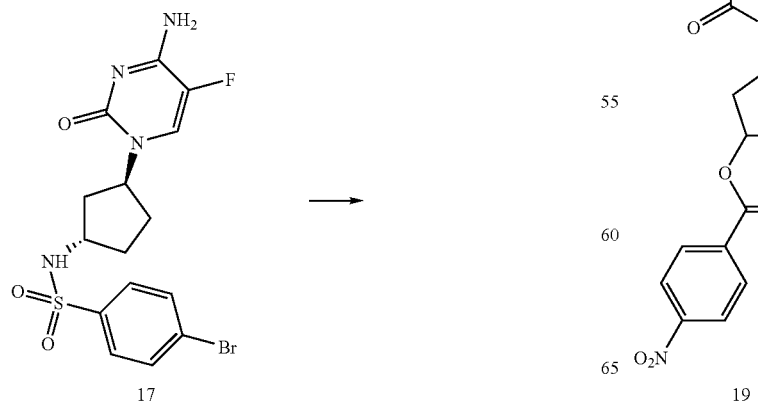

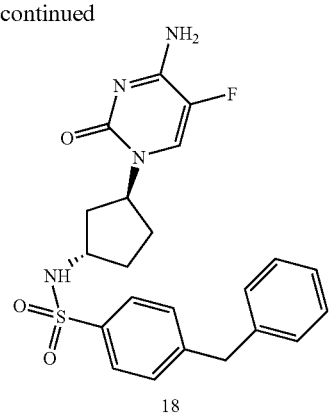

The bromide intermediate 17 was synthesized using general method A. To a mixture of sulfonamide 17 (25 mg, 0.058 mmol) and 0.5M benzylzinc bromide in THF (2 mL) was added Pd(dppf)Cl$_2$ (2 mg, 0.003 mmol) in a microwave vial. The vial was sealed and the reaction mixture was heated to 120° C. for 10 minutes, filtered and then concentrated in vacuo and purified by preparative HPLC to give 10 mg (39% yield) of sulfonamide 18.

5.7. Preparation of 4-amino-5-fluoro-1-((1S,3S)-3-(isoindolin-2-yl)cyclopentyl)pyrimidin-2(1H)-one The captioned compound was prepared according to Scheme 16, which provides an example of what is referred to herein as General Method G:

Scheme 16

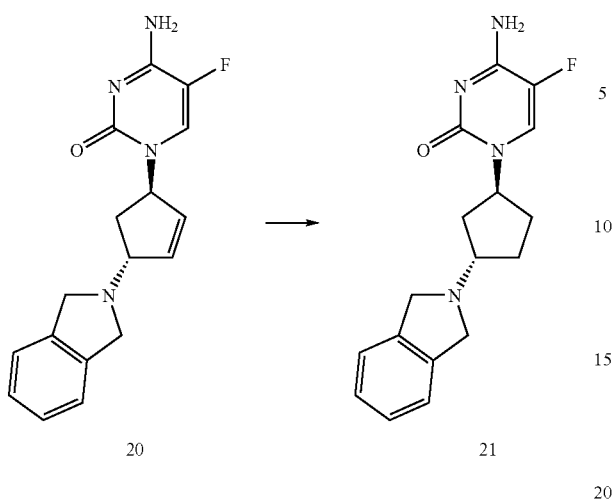

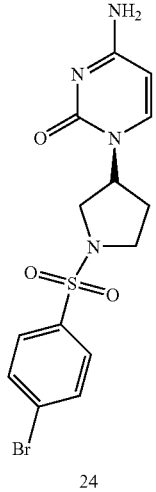

The 4-nitro-benzoate intermediate 19 was synthesized using general method A.

Synthesis of 20: To a mixture of allyic ester 19 (100 mg, 0.28 mmol) in THF (3 mL) was added isoindole (33 mg, 0.28 mmol) and Pd(PPh₃)₄ (16 mg, 0.014 mmol) in a microwave vial. The vial was sealed and heated at 120° C. for 15 minutes and was then filtered and concentrated in vacuo and purified by preparative HPLC to give 28 mg (32% yield) of amine 20. Amine 21 could be subsequently prepared via general method E.

5.8. Preparation of (R)-4-amino-1-(1-(4-bromophenylsulfonyl)-pyrrolidin-3-yl)-1H-pyrimidin-2-one The captioned compound was prepared according to Scheme 17, which provides an example of what is referred to herein as General Method H:

Synthesis of 23: To (R)-3-pyrrolidinol 22 (1.00 g, 11.0 mmol) in 50 mL DCM and 5 mL DIEA was added arylsulphonyl chloride (11.0 mmol) at room temperature. After stirring for 3 hours, methanesulfonyl chloride (0.86 mL, 11.0 mmol) was added and the mixture was stirred for 12 hours. The reaction mixture was extracted with 1N HCl and brine, dried over MgSO₄, and concentrated. Purification on silica gel (EA: 0-100%) gave the product 23 in 80% yield.

Synthesis of 24: Methanesulfonic acid ester 23 (0.262 mmol), K₂CO₃ (40 mg, 0.288 mmol), 18-crown-6 (76 mg, 0.288 mmol), and the cytosine derivative of interest (0.288 mmol) were heated in 1 mL DMF in a sealed tube at 110° C. for 12 hours. The reaction mixture was purified by reversed phase HPLC to give the product 24 as a white solid (10% yield).

Other final targets were prepared using the Suzuki coupling protocol described in General Method A.

5.9. Preparation of (R)-4-Amino-1-[(3S)-1-(biphenyl-4-carbonyl)-pyrrolidin-3-yl]-5-fluoro-1H-pyrimidin-2-one The captioned compound was prepared according to Scheme 18, which provides an example of what is referred to herein as General Method I:

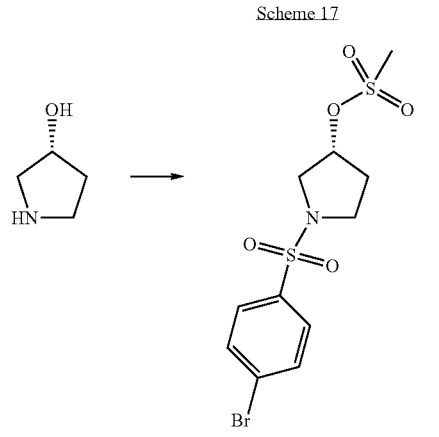

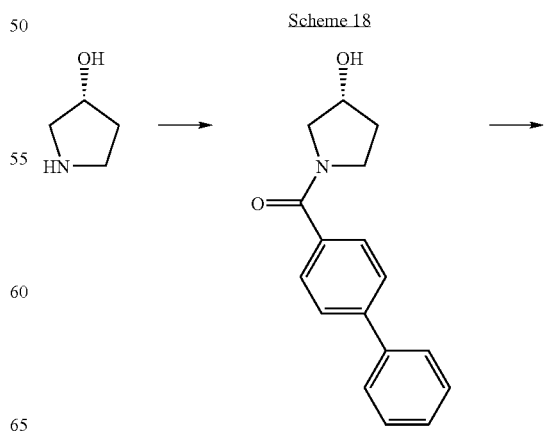

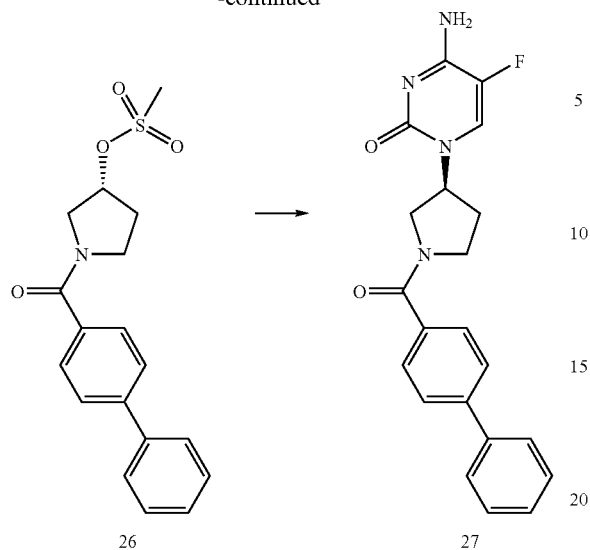

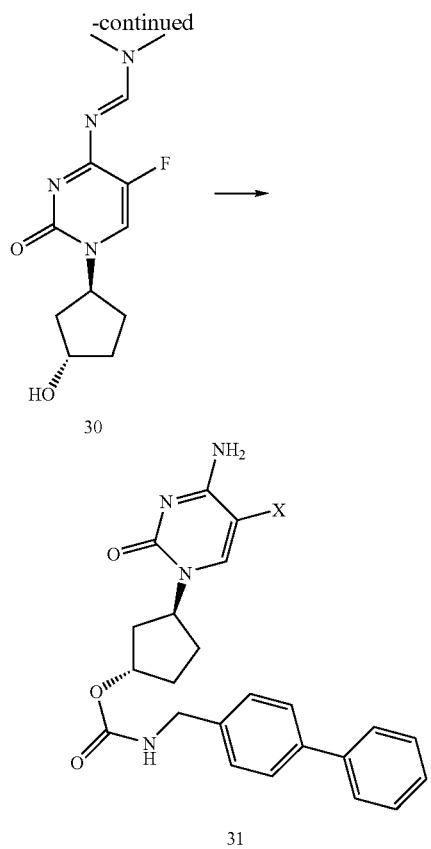

Synthesis of 25: To (R)-3-pyrrolidinol 22 (0.50 g, 5.74 mmol) in 20 mL DCM and 1 mL DIEA was added biphenyl-4-carbonyl chloride (1.24 g, 5.74 mmol) at room temperature. After stirring for 12 hours, the reaction mixture was extracted with 1N HCl and brine, dried over $MgSO_4$, concentrated and purified on silica gel (EA: 100%) to give 25 (400 mg, 1.49 mmol).

Synthesis of 26: To a solution of 25 (400 mg, 1.49 mmol) in 10 mL DCM methanesulfonyl chloride (0.12 mL, 1.49 mmol) was added and the mixture was stirred for 1 hour. The reaction mixture was extracted with 1N HCl and brine, dried over $MgSO_4$, concentrated and purified on silica gel (EA: 100%) to give 26 (201 mg, 0.58 mmol).

Synthesis of 27: A solution of 26 (90 mg, 0.262 mmol), $K_2CO_3$ (40 mg, 0.288 mmol), 18-crown-6 (76 mg, 0.288 mmol), and the 5-fluorocytosine (37 mg, 0.288 mmol) were heated in 1 mL DMF in a sealed tube at 110° C. for 12 hours. The reaction mixture was purified by reversed phase HPLC to give 27 as a white solid (4 mg, 4%).

5.10. Preparation of biphenyl-4-yl-carbamic acid 3-(4-amino-5-fluoro-2-oxo-2H-pyrimidin-1-yl)-cyclopentyl ester The captioned compound was prepared according to Scheme 19, which provides an example of what is referred to herein as General Method J:

Scheme 19

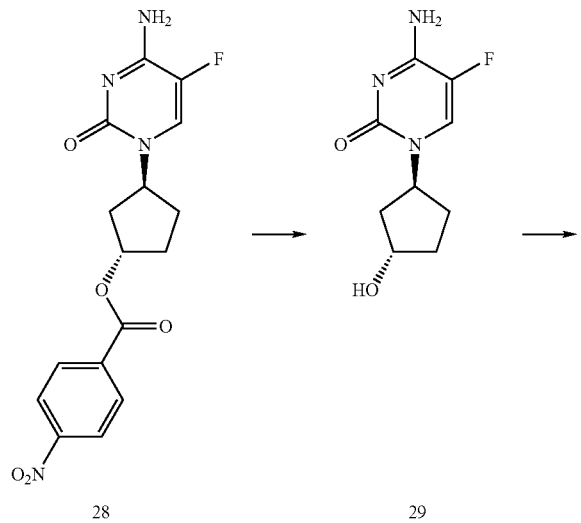

Synthesis of 28: 4-Amino-5-fluoro-1-(3-hydroxy-cyclopentyl)-1H-pyrimidin-2-one was inverted via the Mitsunobu reaction (General Method A) with 4-nitrobenzoic acid to provide 4-nitro-benzoic acid 3-(4-amino-5-fluoro-2-oxo-2H-pyrimidin-1-yl)-cyclopentyl ester 28.

Synthesis of 29: A solution of 4-Nitro-benzoic acid 3-(4-amino-5-fluoro-2-oxo-2H-pyrimidin-1-yl)-cyclopentyl ester (1.27 g, 3.50 mmol) in anhydrous sodium methoxide (0.5 M in methanol, 20 mL, 10 mmol). The mixture was stirred under nitrogen at room temperature for 2 hours, and the solvent was removed in vacuo. The residue was dry-loaded onto silica gel and purified by silica gel plug filtration (20 g $SiO_2$, $CH_2Cl_2$/Methanol/ammonium hydroxide: 88/12/0.25) to afford 4-Amino-5-fluoro-1-(3-hydroxy-cyclopentyl)-1H-pyrimidin-2-one 29 as an off-white solid (0.346 g, 46%).

Synthesis of 30

A solution of 4-amino-5-fluoro-1-(3-hydroxy-cyclopentyl)-1H-pyrimidin-2-one (0.346 g, 1.62 mmol) in anhydrous dimethylformamide (3 mL) was treated with dimethylformamide dimethyl acetal (3 mL). The mixture was stirred at room temperature under nitrogen for 12 hours, concentrated in vacuo, loaded on silica gel, and chromatographed on silica gel (3×7 cm $SiO_2$, 4:1 ethyl acetate/methanol) to afford N'-[5-Fluoro-1-(3-hydroxy-cyclopentyl)-2-oxo-1,2-dihydro-pyrimidin-4-yl]-N,N-dimethyl-formamidine 30 as a milky white oil (0.361 g, 83%).

Synthesis of 31

A solution of N'-[5-fluoro-1-(3-hydroxy-cyclopentyl)-2-oxo-1,2-dihydro-pyrimidin-4-yl]-N,N-dimethyl-formamidine (0.050 g, 0.186 mmol) in $CH_2Cl_2$ (2 mL) and anhydrous dimethylformamide (1 mL) was treated with 4-biphenyl isocyanate (0.039 g, 0.2 mmol). The mixture was stirred at room temperature under nitrogen for 5 hours, then quenched by the addition of acetic acid (0.5 mL) and stirred 10 minutes. The mixture was concentrated in vacuo, loaded on silica gel, and chromatographed on silica gel (10 g $SiO_2$, 8:1 ethyl acetate/methanol) to afford biphenyl-4-yl-carbamic acid 3-(4-amino-5-fluoro-2-oxo-2H-pyrimidin-1-yl)-cyclopentyl ester 31 as a white solid (0.029 g, 38%).

5.11. Preparation of biphenyl-3-sulfonic acid [3-(4-amino-5-fluoro-2-oxo-2H-pyrimidin-1-yl)-cyclopentyl]-amide The captioned compound was prepared according to Scheme 20, which provides an example of what is referred to herein as General Method K:

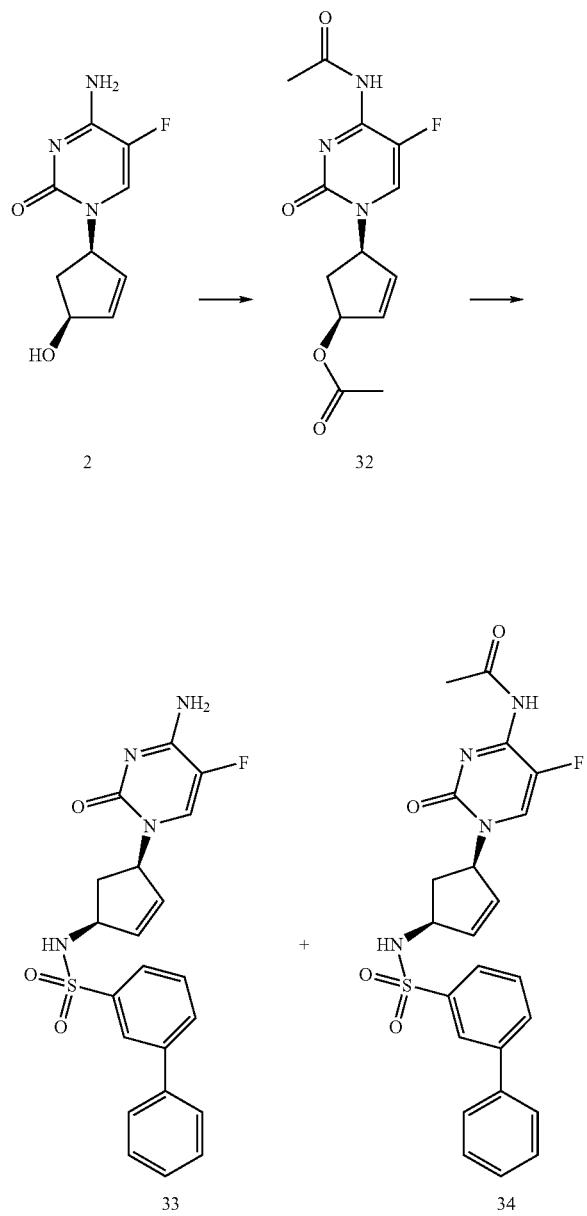

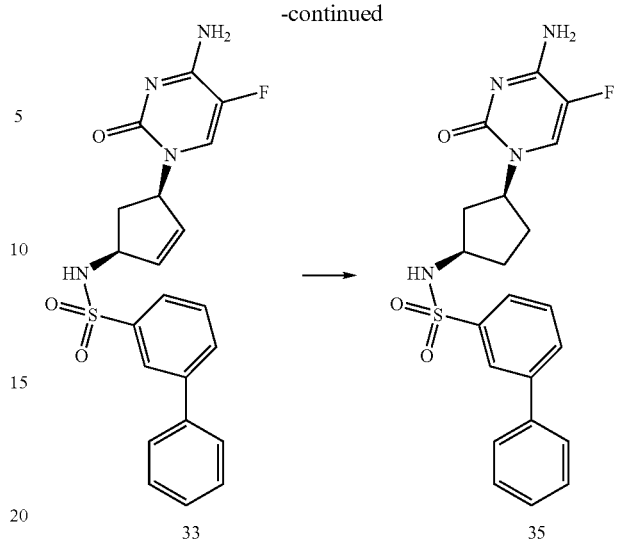

Synthesis of 33 and 34: A solution of acetic acid 4-(4-acetylamino-5-fluoro-2-oxo-2H-pyrimidin-1-yl)-cyclopent-2-enyl ester 32 (0.543 g, 1.84 mmol) in anhydrous tetrahydrofuran (10 mL) was treated with tetrakis triphenylphosphine palladium (0) (0.10 g, 0.09 mmol). The mixture was degassed under nitrogen for 10 minutes, then treated with a solution of the sodium anion of 4-biphenylsulfonamide (anion was generated by treating a solution of 4-biphenylsulfonamide (0.0.699 g, 3.0 mmol) in DMF (10 mL) with sodium hydride (0.076 g, 3.0 mmol) and allowing to stir 10 minutes until gas evolution ceased). After treatment of sulfonamide anion with pi-allyl complex, the mixture was heated to 60° C. for 2 hours (or 120° C. for 10 minutes via microwave). The mixture was concentrated in vacuo, taken up in methanol (5 mL), and stirred over catalytic potassium carbonate, then purified by silica gel column (9:1 ethyl acetate/methanol) followed by preparative HPLC (20-60% ammonium acetate/ACN, Sunfire C18 column) to afford biphenyl-3-sulfonic acid [4-(4-amino-5-fluoro-2-oxo-2H-pyrimidin-1-yl)-cyclopent-2-enyl]-amide 33 as a white solid (0.130 g, 21%). The side product N-{1-[4-(Biphenyl-3-sulfonylamino)-cyclopent-2-enyl]-5-fluoro-2-oxo-1,2-dihydro-pyrimidin-4-yl}-acetamide 34 was also isolated as a white solid (0.006 g, 1%).

Synthesis of 35: Biphenyl-3-sulfonic acid [4-(4-amino-5-fluoro-2-oxo-2H-pyrimidin-1-yl)-cyclopent-2-enyl]-amide was reduced via General Method E to provide Biphenyl-3-sulfonic acid [3-(4-amino-5-fluoro-2-oxo-2H-pyrimidin-1-yl)-cyclopentyl]-amide 35.

5.12. Characterization of Representative Compounds

Specific compounds were prepared using the general methods described above, and were characterized by various methods, including high performance liquid chromatography (HPLC), molecular weight and proton NMR.

The HPLC protocols used were:
Method A: Column=Shim VP ODS 4.6×50 mm; Start % B=0; Final % B=100; Gradient time=3 min, 3 min stop; Flow rate=3.5 mL/min; Solvent A=90:10 water/methanol w/0.1% TFA; Solvent B=90: 10 MeOH/water w/0.1% TFA; Observation Wavelength=220 nm.
Method B: Column=Sunfire C18 5u 4.6×50 mm; Start % B=0; Final % B=100; Gradient time=2 min, 3 min stop; Flow rate=3.5 mL/min; Solvent A=10 mM NH₄OAc; Solvent B=MeCN; Observation Wavelength=254 nm.

Method C: Column=Sunfire C18 5u 4.6×50 mm; Start % B=0; Final % B=100; Gradient time=2 min, 3 min stop; Flow rate=3.5 mL/min; Solvent A=10 mM NH₄OAc; Solvent B=MeCN; Observation Wavelength=220 and 254 nm.

Method D: Column=Neutral Sunfire ODS 4.6×50 mm; Start % B=0; Final % B=100; Gradient time=4 min; 5 min stop; Flow rate=3.5 mL/min; Solvent A=10 mM NH₄OAc; Solvent B=MeCN; Observation Wavelength=220 and 254 nm.

Method E: Column=Luna Phenylhexyl 5u 4.6×50 mm; Start % B=0; Final % B=100; Gradient time=3 min; 4 min stop; Flow rate=3 mL/min; Solvent A=10 mM NH₄OAc; Solvent B=MeCN; Observation Wavelength=220 and 254 nm.

Method F: Column=Luna Phenylhexyl 5u 4.6×50 mm; Start % B=0; Final % B=100; Gradient time=4 min, 5 min stop; Flow rate=2 mL/min; Solvent A=10 mM NH₄OAc; Solvent B=MeCN; Observation Wavelength=220 and 254 nm.

Method G: Column=Luna Phenylhexyl C18 3 μm 4.6 mm ID×50 mm. 10 to 95% B over 2.0 min; 3 min stop; Flow rate=4.5 mL/min; 45 degC; Solvent A=10 mM NH₄OAc; Solvent B=MeCN; Observation Wavelength=220, 250 nm Method H: Column=Sunfire C18 5u 4.6×50 mm; Start % B=20; Final % B=60; Gradient time=2 min, 3 min stop; Flow rate=3.5 mL/min; Solvent A=10 mM NH₄OAc; Solvent B=MeCN; Observation Wavelength=220 and 254 nm.

Method I: Column=Sunfire C18 5u 4.6×50 mm; Start % B=20; Final % B=50; Gradient time=2 min, 3 min stop; Flow rate=3.5 mL/min; Solvent A=10 mM NH₄OAc; Solvent B=MeCN; Observation Wavelength=220 and 254 nm.

Method J: Column=Sunfire C18 5u 4.6×50 mm; Start % B=0; Final % B=60; Gradient time=2 min, 3 min stop; Flow rate=3.5 mL/min; Solvent A=10 mM NH₄OAc; Solvent B MeCN; Observation Wavelength=220 and 254 nm.

Method K: Column=Sunfire C18 5u 4.6×50 mm; Start % B=0; Final % B=100; Gradient time=2 min, 3 min stop; Flow rate=3.5 mL/min; Solvent A=90:10 H₂O/MeOH with 0.1% TFA; Solvent B=10:90 H₂O/MeOH with 0.1% TFA; Observation Wavelength 220 and 254 nm.

Method L: Column=Shim-Pack VP ODS 4.6×50 mm, Start % B=0; Final % B=100; Gradient time=4 min, 5 min stop; Flow rate=3.0 mL/min; Solvent A=10 mM NH₄OAc; Solvent B=MeCN; Observation Wavelength=220 and 254 nm.

Method M: Column=Sunfire C18 5u 4.6×50 mm; Start % B=0 Final % B=50 Gradient time=10 min, Flow rate=3.5 mL Solvent A=10 mM NH₄OAc Solvent B=MeCN: 10 mM NH₄OAc; Observation Wavelength=220 nM, 250 nm.

Method N: Column=Sunfire C18 5u 4.6×50 mm Start % B=20; Final % B=70 Gradient time=10 min; Flow rate=3.5 ml/min; Solvent A=10 mM NH₄+OAc-Solvent B=MeCN; Observation Wavelength=254 and 220 nm.

Method 0: Column=Sunfire C18 5u 4.6×50 mm; Solvent A=10 mM NH₄OAc Solvent B=MeCN % B (start)=0 100% at 3 min; Flow rate=3.5 mL/min; Observation Wavelength=220 and 254 nm.

Method P: Column=Sunfire C18 5u 4.6×50 mm Start % B=10; Final % B=100 Gradient time=2 min; Flow rate=3.5 ml/min Solvent A=10 mM NH₄OAc; Solvent B=MeCN; Observation Wavelength=220-400 nm.

Method Q: Column=Xterra Phenyl 5 μm 4.6×50 mm; Solvent A=10 mM NH₄OAc; Solvent B=MeCN; 0-100% B over 5 min; Flow rate=2.5 mL/min; Observation Wavelength=254, 290 nm.

Method R: Column=Sunfire C18 3.5 μm 4.6 mm ID×50 mm; 10 to 95% B over 2.0 min; 3 min stop; Flow rate=4.5 mL/min; 45° C.; Solvent A=10 mM NH₄OAc; Solvent B=MeCN; Observation Wavelength=220, 250 nm.

Method S: Column=Sunfire C18 5 μm 4.6×50 mm; Start % B=10; Final % B=90; Gradient time=6 min, 8 min stop; Flow rate=3.5 mL/min; Solvent A=10 mM NH₄OAc; Solvent B=MeCN; Observation Wavelength=220, 254 nm.

Characteristics of various specific compounds are set forth below in Table 8. The general synthetic method used to make a particular compound is provided in the "Synth" column. The HPLC retention time was measured in minutes. The MW column includes the calculated molecular weight and the observed molecular weight in parenthesis. Proton NMR data for select compounds is provided in the last column.

TABLE 8

| Chemical Name | Synth. | Calc. Mol. Wt. (Obs. Mol. Wt.) | HPLC Method (Time) | ¹H NMR |
|---|---|---|---|---|
| 4-[(1S,3S)-3-(4-Amino-5-fluoro-2-oxo-2H-pyrimidin-1-yl)-cyclopentylsulfamoyl]-N-phenyl-benzamide | D | 471.51 (472.2) | L (2.540) | |
| 4-[(1S,3S)-3-(4-Amino-5-fluoro-2-oxo-2H-pyrimidin-1-yl)-cyclopentylsulfamoyl]-N-cyclohexyl-benzamide | D | 477.55 (478.3) | L (2.155) | |
| 4-[(1S,3S)-3-(4-Amino-5-fluoro-2-oxo-2H-pyrimidin-1-yl)-cyclopentylsulfamoyl]-N-(2-morpholin-4-yl-ethyl)-benzamide | D | 508.57 (509.0) | L (1.587) | (400 MHz, CD₃OD) δ: 1.50 (m, 1H), 1.70 (m, 1H), 1.85 (m, 2H), 1.94 (br, 3H), 2.070 (m, 2H), 2.54 (br, 3H), 2.62 (t, J = 6.8 Hz, 1H), 3.56 (t, J = 6.4 Hz, 2H), 3.70 (t, J = 4.8 Hz, 3H), 3.918 (m, 1H), 4.84 (m, 1H), 7.75 (d, J = 6.8 Hz, 1H), 7.65 (m, 4H) |

TABLE 8-continued

| Chemical Name | Synth. | Calc. Mol. Wt. (Obs. Mol. Wt.) | HPLC Method (Time) | [1] H NMR |
|---|---|---|---|---|
| 4-[(1S,3S)-3-(4-Amino-5-fluoro-2-oxo-2H-pyrimidin-1-yl)-cyclopentylsulfamoyl]-N-isopropyl-benzamide | D | 437.49 (437.9) | L (1.787) | |
| 4-[(1S,3S)-3-(4-Amino-5-fluoro-2-oxo-2H-pyrimidin-1-yl)-cyclopentylsulfamoyl]-N-(4-tert-butyl-thiazol-2-yl)-benzamide | D | 534.63 (534.9) | L (2.640) | |
| 4-[(1S,3S)-3-(4-Amino-5-fluoro-2-oxo-2H-pyrimidin-1-yl)-cyclopentylsulfamoyl]-N-(5-methyl-thiazol-2-yl)-benzamide | D | 492.55 (492.9) | L (2.098) | |
| 4-[(1S,3S)-3-(4-Amino-5-fluoro-2-oxo-2H-pyrimidin-1-yl)-cyclopentylsulfamoyl]-N-[1,3,4]thiadiazol-2-yl-benzamide | D | 479.51 (479.9) | L (1.735) | |
| 3-[(1S,3S)-3-(4-Amino-5-fluoro-2-oxo-2H-pyrimidin-1-yl)-cyclopentylsulfamoyl]-N-(4-tert-butyl-thiazol-2-yl)-benzamide | D | 534.63 (535.0) | L (2.588) | (300 MHz, $CD_3OD$) δ: 1.380 (s, 9H), 1.55 (m, 1H), 1.79 (m, 1H), 2.00 (t, J = 6.8 Hz, 2H), 2.12 (m, 2H), 3.97 (m, J = 7 Hz, 1H), 4.88 (m, 1H), 6.83 (s, 1H), 7.77 (t, J = 8 Hz, 1H), 8.13 (d, J = 8 Hz, 1H), 8.30 (m, 2H), 8.56 (s, 1H) |
| 2-[(S)-3-((S)-4-Amino-5-fluoro-2-oxo-2H-pyrimidin-1-yl)-cyclopentyl]-isoindole-1,3-dione | B | 342.32 (343.0) | F (2.295) | (300 MHz, MeOD) δ: 1.80-1.90 (m, 1H), 2.01-2.22 (m, 4H), 2.37-2.47 (m, 1H), 4.80-4.92 (m, 1H), 5.20-5.27 (m, 1H), 7.68-7.77 (m, 4H), 7.86 (d, J = 9 Hz, 1H) |
| 2-[(S)-3-((S)-4-Amino-5-fluoro-2-oxo-2H-pyrimidin-1-yl)-cyclopentyl]-5-nitro-isoindole-1,3-dione | B | 387.32 (388.0) | E (1.797) | |
| 6-[(S)-3-((S)-4-Amino-5-fluoro-2-oxo-2H-pyrimidin-1-yl)-cyclopentyl]-pyrrolo[3,4-b]pyridine-5,7-dione | B | 343.31 (344.0) | E (1.448) | |
| 2-[(S)-3-((S)-4-Amino-5-fluoro-2-oxo-2H-pyrimidin-1-yl)-cyclopentyl]-pyrrolo[3,4-c]pyridine-1,3-dione | B | 343.31 (344.0) | F (1.625) | (300 MHz, MeOD) δ: 1.85-1.91 (m, 1H), 2.00-2.22 (m, 4H), 2.38-2.48 (m, 1H), 4.86-4.98 (m, 1H), 5.15-5.27 (m, 1H), 7.75 (d, J = 9.0 Hz, 1H), 7.85 (d, J = 6.9 Hz, 1H), 8.92-8.98 (m, 2H) |
| Biphenyl-4-carboxylic acid [(S)-3-((S)-4-amino-5-fluoro-2-oxo-2H-pyrimidin-1-yl)-cyclopentyl]-amide | B | 392.43 (393.0) | F (2.223) | |
| 5-Phenyl-furan-2-carboxylic acid [(S)-3-((S)-4-amino-5-fluoro-2-oxo-2H-pyrimidin-1-yl)-cyclopentyl]-amide | B | 382.39 (383.0) | F (2.093) | (400 MHz, $CDCl_3$) δ: 1.65-1.75 (m, 2H), 2.00-2.37 (m, 4H), 4.51-4.58 (m, 1H), 4.90-5.05 (m, 1H), 6.82 (d, J = 3.6 Hz, 1H), 7.11 (d, J = 3.6 Hz, 1H), 7.21-7.38 (m, 3H), 7.78-7.86 (m, 3H) |
| 4'-Cyano-biphenyl-4-carboxylic acid [(S)-3-((S)-4-amino-5-fluoro-2-oxo-2H-pyrimidin-1-yl)-cyclopentyl]-amide | B | 417.44 (418.0) | F (2.130) | (300 MHz, MeOD) δ: 1.67-2.28 (m, 6H), 4.50-4.57 (m, 1H), 4.91-5.00 (m, 1H), 6.92 (d, J = 7.8 Hz, 2H), 7.60-7.95 (m, 9H) |

TABLE 8-continued

| Chemical Name | Synth. | Calc. Mol. Wt. (Obs. Mol. Wt.) | HPLC Method (Time) | ¹H NMR |
|---|---|---|---|---|
| 3',5'-Dichloro-biphenyl-4-carboxylic acid [(S)-3-((S)-4-amino-5-fluoro-2-oxo-2H-pyrimidin-1-yl)-cyclopentyl]-amide | B | 461.32 (462.0) | F (2.960) | (300 MHz, MeOD) δ: 1.79-2.01 (m, 2H), 2.17-2.35 (m, 4H), 4.60-4.70 (m, 1H), 5.05-5.14 (m, 1H), 7.50 (s, 1H), 7.68 (s, 2H), 7.76 (d, J = 8.7 Hz, 2H), 7.96 (d, J = 8.7 Hz, 2H), 8.22 (d, J = 6.6 Hz, 1H) |
| 4'-Methyl-biphenyl-4-carboxylic acid [(S)-3-((S)-4-amino-5-fluoro-2-oxo-2H-pyrimidin-1-yl)-cyclopentyl]-amide | B | 406.45 (407.0) | F (2.338) | |
| N-[(S)-3-((S)-4-Amino-5-fluoro-2-oxo-2H-pyrimidin-1-yl)-cyclopentyl]-4-phenoxy-benzamide | B | 408.43 (409.0) | E (1.872) | (300 MHz, MeOD) δ: 1.63-1.73 (m, 2H), 2.00-2.25 (m, 4H), 4.46-4.54 (m, 1H), 4.94-5.02 (m, 1H), 6.80-6.97 (m, 4H), 7.12 (dd, J = 6.6 Hz, 1H), 7.28-7.34 (m, 2H), 7.73 (dd, J = 2.1, 6.6 Hz, 1H), 7.83 (d, J = 6.9 Hz, 1H) |
| N-[(S)-3-((S)-4-Amino-5-fluoro-2-oxo-2H-pyrimidin-1-yl)-cyclopentyl]-3-phenoxy-benzamide | B | 408.43 (409.0) | G (1.120) | (300 MHz, MeOD) δ: 1.62-1.80 (m, 2H), 2.00-2.25 (m, 4H), 4.46-4.54 (m, 1H), 4.91-5.00 (m, 1H), 6.92 (d, J = 7.8 Hz, 2H), 7.02-7.07 (m, 2H), 7.25-7.38 (m, 4H), 7.48 (d, J = 7.5 Hz, 1H), 7.82 (d, J = 6.9 Hz, 1H) |
| 1H-Benzoimidazole-2-carboxylic acid [(S)-3-((S)-4-amino-5-fluoro-2-oxo-2H-pyrimidin-1-yl)-cyclopentyl]-amide | B | 356.35 (357.0) | E (1.478) | (400 MHz, CDCl₃) δ: 1.65-186 (m, 2H), 2.05-2.31 (m, 4H), 4.51-4.60 (m, 1H), 4.90-5.05 (m, 1H), 7.19-7.27 (m, 2H), 7.46-7.66 (m, 2H), 7.83 (d, J = 6 Hz, 1H) |
| 5-Phenyl-1H-pyrrole-2-carboxylic acid [(S)-3-((S)-4-amino-5-fluoro-2-oxo-2H-pyrimidin-1-yl)-cyclopentyl]-amide | B | 381.40 (382.0) | E (1.762) | (300 MHz, MeOD) δ: 1.60-1.79 (m, 2H), 2.01-2.28 (m, 4H), 4.47-4.54 (m, 1H), 4.97-5.04 (m, 1H), 6.44 (d, J = 3.9 Hz, 1H), 6.82 (d, J = 3.9 Hz, 1H), 7.15 (dd, J = 7.2, 7.2 Hz, 1H), 7.29 (dd, J = 7.8, 7.8 Hz, 2H), 7.57 (d, J = 8.1 Hz 2H), 7.84 (d, J = 6.9 Hz, 1) |
| 1,2,3,4,4a,8a-Hexahydro-naphthalene-1-carboxylic acid [(S)-3-((S)-4-amino-5-fluoro-2-oxo-2H-pyrimidin-1-yl)-cyclopentyl]-amide | B | 370.42 (371.0) | E (1.640) | (300 MHz, MeOD) δ: 1.54-2.18 (m, 10H), 2.67-2.74 (m, 2H), 3.57-3.61 (m, 1H), 4.30-4.34 (m, 1H), 4.80-5.01 (m, 1H), 6.95-7.01 (m, 4H), 7.80 (d, J = 6.0 Hz, 1H), |
| N-[(S)-3-((S)-4-Amino-5-fluoro-2-oxo-2H-pyrimidin-1-yl)-cyclopentyl]-3-bromo-benzamide | B | 395.23 (395 and 397) | E (1.687) | |
| N-[(S)-3-((S)-4-Amino-5-fluoro-2-oxo-2H-pyrimidin-1-yl)-cyclopentyl]-3-pyridin-4-yl-benzamide | B | 393.41 (394.0) | E (1.558) | (300 MHz, MeOD) δ: 1.64-2.3 (m, 6H), 4.50-4.60 (m, 1H), 4.92-5.03 (m, 1H), 7.49-7.55 (m, 1H), 7.68 (d, J = 6.0 Hz, 2H), 7.83 (d, J = 6.9 Hz, 2H), 8.12 (s, 1H), 8.51 (d, J = 5.7 Hz, 1H) |
| Biphenyl-3-carboxylic acid [(S)-3-((S)-4-amino-5-fluoro-2-oxo-2H-pyrimidin-1-yl)-cyclopentyl]-amide | B | 392.43 (393.0) | E (1.875) | |

TABLE 8-continued

| Chemical Name | Synth. | Calc. Mol. Wt. (Obs. Mol. Wt.) | HPLC Method (Time) | $^1$H NMR |
|---|---|---|---|---|
| 4'-Chloro-biphenyl-3-carboxylic acid [(S)-3-((S)-4-amino-5-fluoro-2-oxo-2H-pyrimidin-1-yl)-cyclopentyl]-amide | B | 426.87 (427.0) | E (2.023) | (300 MHz, MeOD) δ: 1.78-2.40 (m, 6H), 4.60-4.70 (m, 1H), 5.05-5.20 (m, 1H), 7.45-7.60 (m, 3H), 7.69 (d, J = 8.4 Hz, 2H), 7.80-7.86 (m, 1H), 7.95 (d, J = 6.6 Hz, 1H), 8.092 (s, 1H) |
| 4'-Cyano-biphenyl-3-carboxylic acid [(S)-3-((S)-4-amino-5-fluoro-2-oxo-2H-pyrimidin-1-yl)-cyclopentyl]-amide | B | 417.44 (418.0) | E (1.810) | |
| Naphthalene-2-carboxylic acid [(S)-3-((S)-4-amino-5-fluoro-2-oxo-2H-pyrimidin-1-yl)-cyclopentyl]-amide | B | 366.39 (367.0) | E (1.720) | (300 MHz, MeOD) δ: 1.67-1.85 (m, 2H), 2.06-2.30 (m, 4H), 4.43-4.60 (m, 1H), 4.99-5.06 (m, 1H), 7.44-7.52 (m, 2H), 7.77-7.91 (m, 5H), 8.30 (s, 1H) |
| tert-butyl (1S,3S)-3-(4-amino-2-oxopyrimidin-1(2H)-yl)cyclopentyl(3'-chlorobiphenyl-3-ylsulfonyl)carbamate | A | 545.05 (545.0) | C (1.803) | (400 MHz, CD$_3$OD) δ: 1.25 (s, 9H), 2.0-2.2 (m, 5H), 2.34 (m, 1H), 5.08 (m, 1H), 5.18 (m, 1H), 5.79 (d, J = 10.0 Hz, 1H), 7.35 (m, 3H), 7.49 (m, 1H), 7.58 (m, 4H), 7.79 (d, J = 10.6 Hz, 1H), 7.84 (d, J = 10.6 Hz, 1H), 8.00 (m, 1H) |
| 4'-Chloro-biphenyl-4-sulfonic acid [(1S,3S)-3-(4-amino-5-fluoro-2-oxo-2H-pyrimidin-1-yl)-cyclopentyl]-amide | A | 462.93 (463.0) | B (1.547) | |
| 2',3'-Difluoro-biphenyl-4-sulfonic acid [(1S,3S)-3-(4-amino-5-fluoro-2-oxo-2H-pyrimidin-1-yl)-cyclopentyl]-amide | A | 464.46 (465.1) | B (1.497) | |
| N-[(1S,3S)-3-(4-Amino-5-fluoro-2-oxo-2H-pyrimidin-1-yl)-cyclopentyl]-4-benzo[1,3]dioxol-5-yl-benzenesulfonamide | A | 472.49 (473.1) | B (1.425) | |
| N-[(1S,3S)-3-(4-Amino-5-fluoro-2-oxo-2H-pyrimidin-1-yl)-cyclopentyl]-4-methyl-benzenesulfonamide | A | 366.41 (367.4) | E (1.460) | |
| N-[(1S,3S)-3-(4-Amino-5-fluoro-2-oxo-2H-pyrimidin-1-yl)-cyclopentyl]-3-chloro-benzenesulfonamide | A | 386.83 (387.8) | E (1.460) | |
| N-[(1S,3S)-3-(4-Amino-5-fluoro-2-oxo-2H-pyrimidin-1-yl)-cyclopentyl]-benzenesulfonamide | A | 352.39 (353.3) | E (1.250) | |
| N-[(1S,3S)-3-(4-Amino-5-fluoro-2-oxo-2H-pyrimidin-1-yl)-cyclopentyl]-4-bromo-benzenesulfonamide | A | 431.28 (431.2 and 433.2) | E (1.220) | |
| N-((1S,3S)-3-(4-amino-5-fluoro-2-oxopyrimidin-1(2H)-yl)cyclopentyl)biphenyl-4-sulfonamide | A | 428.48 (429.4) | E (1.760) | |
| N-((1S,3S)-3-(4-amino-5-fluoro-2-oxopyrimidin-1(2H)-yl)cyclopentyl)-4-(pyrimidin-5-yl)benzenesulfonamide | A | 430.46 (431.4) | E (1.140) | |
| N-((1S,3S)-3-(4-amino-5-fluoro-2-oxopyrimidin-1(2H)-yl)cyclopentyl)-4-fluorobenzenesulfonamide | A | 446.47 (447.4) | E (2.000) | |
| N-[(1S,3S)-3-(4-Amino-5-fluoro-2-oxo-2H-pyrimidin-1-yl)-cyclopentyl]-4-(2-methoxy-pyrimidin-5-yl)-benzenesulfonamide | A | 460.48 (461.4) | E (1.200) | |

TABLE 8-continued

| Chemical Name | Synth. | Calc. Mol. Wt. (Obs. Mol. Wt.) | HPLC Method (Time) | $^1$H NMR |
|---|---|---|---|---|
| Biphenyl-3-sulfonic acid [(1S,3S)-3-(4-amino-5-fluoro-2-oxo-2H-pyrimidin-1-yl)-cyclopentyl]-amide | A | 428.48 (429.4) | E (1.320) | |
| 4'-Cyano-biphenyl-4-sulfonic acid [(S)-3-((S)-4-amino-5-fluoro-2-oxo-2H-pyrimidin-1-yl)-cyclopentyl]-amide | A | 453.49 (454.0) | F (2.267) | |
| 4'-Trifluoromethyl-biphenyl-4-sulfonic acid [(S)-3-((S)-4-amino-5-fluoro-2-oxo-2H-pyrimidin-1-yl)-cyclopentyl]-amide | A | 496.48 (497.0) | F (2.590) | |
| 4'-Methyl-biphenyl-4-sulfonic acid [(S)-3-((S)-4-amino-5-fluoro-2-oxo-2H-pyrimidin-1-yl)-cyclopentyl]-amide | A | 442.51 (443.0) | E (2.033) | |
| 2'-Chloro-biphenyl-4-sulfonic acid [(1S,3S)-3-(4-amino-5-fluoro-2-oxo-2H-pyrimidin-1-yl)-cyclopentyl]-amide | A | 462.93 (463.1) | C (1.490) | (400 MHz, CD$_3$OD) δ: 1.54 (m, 1H), 1.71 (m, 1H), 1.90 (m, 2H), 2.1 (m, 2H), 3.92 (t, J = 6.8 Hz, 1H), 4.84 (m, 1H), 7.39 (m, 4H), 7.52 (m, 1H), 7.62 (m, 2H), 7.76 (d, J = 6.8 Hz, 1H), 7.94 (m, 2H) |
| tert-butyl (1S,3S)-3-(4-amino-2-oxopyrimidin-1(2H)-yl)cyclopentyl(3-bromophenylsulfonyl)carbamate | A | 513.41 (513.0) | J (2.550) | |
| Biphenyl-3-sulfonic acid [(1S,3S)-3-(4-amino-2-oxo-2H-pyrimidin-1-yl)-cyclopentyl]-amide | A | 410.49 (411.2) | C (1.390) | |
| N-[(1S,3S)-3-(4-Amino-2-oxo-2H-pyrimidin-1-yl)-cyclopentyl]-3-bromo-benzenesulfonamide | A | 413.29 (414.0) | C (1.710) | |
| 4'-Chloro-biphenyl-3-sulfonic acid [(1S,3S)-3-(4-amino-2-oxo-2H-pyrimidin-1-yl)-cyclopentyl]-amide | A | 444.94 (445.1) | C (1.500) | (400 MHz, CD$_3$OD) δ: 1.54 (m, 1H), 1.71 (m, 1H), 1.90 (m, 2H), 2.05 (m, 2H), 3.923 (m, 1H), 4.82 (m, 1H), 5.81 (d, J = 7.6 Hz, 1H), 7.50 (m, 3H), 7.65 (m, 3H), 7.85 (d, J = 7.6 Hz, 2H), 8.10 (m, 1H) |
| 2'-Chloro-biphenyl-3-sulfonic acid [(1S,3S)-3-(4-amino-2-oxo-2H-pyrimidin-1-yl)-cyclopentyl]-amide | A | 444.94 (445.1) | C (1.440) | |
| 4'-Chloro-3'-methyl-biphenyl-3-sulfonic acid [(1S,3S)-3-(4-amino-2-oxo-2H-pyrimidin-1-yl)-cyclopentyl]-amide | A | 458.96 (458.9) | C (1.578) | |
| 4'-Trifluoromethoxy-biphenyl-3-sulfonic acid [(1S,3S)-3-(4-amino-2-oxo-2H-pyrimidin-1-yl)-cyclopentyl]-amide | A | 494.49 (494.9) | C (1.410) | |
| 3'-Chloro-biphenyl-3-sulfonic acid [(1S,3S)-3-(4-amino-2-oxo-2H-pyrimidin-1-yl)-cyclopentyl]-amide | A | 444.94 (445.0) | C (1.470) | (400 MHz, CDCl$_3$) δ: 1.52 (m, 1H), 1.78 (m, 1H), 1.84-2.01 (m, 4H), 3.67 (m, 1H), 3.95 (m, 1H), 5.84 (d, J = 9.6 Hz, 1H), 7.41-7.69 (m, 6H), 7.90 (m, 1H), 8.11 (s, 1H) |
| 2'-Methyl-biphenyl-4-sulfonic acid [(1S,3S)-3-(4-amino-5-fluoro-2-oxo-2H-pyrimidin-1-yl)-cyclopentyl]-amide | A | 442.51 (443.1) | C (1.490) | |

TABLE 8-continued

| Chemical Name | Synth. | Calc. Mol. Wt. (Obs. Mol. Wt.) | HPLC Method (Time) | ¹H NMR |
|---|---|---|---|---|
| 4'-tert-Butyl-biphenyl-4-sulfonic acid [(1S,3S)-3-(4-amino-5-fluoro-2-oxo-2H-pyrimidin-1-yl)-cyclopentyl]-amide | A | 484.59 (485.2) | K (2.137) | (400 MHz, CD$_3$OD) δ: 1.35 (s, 9H); 1.54 (m, 1H); 1.69 (m, 1H); 1.92 (m, 2H); 2.07 (m, 2H); 3.91 (m, 1H); 4.84 (m, 1H); 7.52 m, 2H); 7.63 (m, 2H); 7.76 (d, 1H, J = 6.7 Hz); 7.81 (m, 2H); 7.93 (m, 2H) |
| 3'-Chloro-biphenyl-4-sulfonic acid [(1S,3S)-3-(4-amino-5-fluoro-2-oxo-2H-pyrimidin-1-yl)-cyclopentyl]-amide | A | 462.93 (463.0) | L (2.585) | (400 MHz, CD$_3$OD) δ: 1.534 (m, 1H), 1.762 (m, 1H), 1.982 (t, J = 8.4 Hz, 2H), 2.052 (m, 1H), 2.135 (m, 1H), 3.886 (t, J = 6.8 Hz, 1H), 4.863 (m, 1H), 7.463 (m, 2H), 7.628 (m, J = 7.6 Hz, 1H), 7.713 (s, 1H), 7.836 (d, J = 8.4, 2H), 7.964 (d, J = 8.4, 2H), 8.278 (d, J = 6.8 Hz, 1H) |
| 2'-Methyl-biphenyl-3-sulfonic acid [(1S,3S)-3-(4-amino-5-fluoro-2-oxo-2H-pyrimidin-1-yl)-cyclopentyl]-amide | A | 442.51 (443.2) | L (2.492) | (400 MHz, CD$_3$OD) δ: 1.529 (m, 1H), 1.708 (m, 1H), 1.881 (t, J = 8.4 Hz, 2H), 2.070 (m, 1H), 2.234 (s, 3H), 3.922 (m, J = 6.8 Hz, 1H), 4.80 (m, 1H), 7.211 (m, 1H), 7.267 (m, 1H), 7.284 (m, 2H), 7.607 (m, 2H), 7.766 (d, J = 6.4 Hz, 1H), 7.803 (s, 1H), 7.872 (d, J = 7.2 Hz, 1H) |
| 3'-Chloro-biphenyl-3-sulfonic acid [(1S,3S)-3-(4-amino-5-fluoro-2-oxo-2H-pyrimidin-1-yl)-cyclopentyl]-amide | A | 462.93 (463.1) | L (2.585) | (400 MHz, CD$_3$OD) δ: 1.522 (m, 1H), 1.708 (m, 1H), 1.898 (t, J = 8.4 Hz, 2H), 2.063 (m, 2H), 3.928 (m, J = 7.2 Hz, 1H), 4.845 (m, 1H), 7.443 (m, 1H), 7.488 (t, J = 8 Hz, 1H), 7.611 (m, J = 8 Hz, 1H), 7.660 (d, J = 8 Hz, 1H), 7.689 (m, 1H), 7.758 (d, J = 6.8, 1H), 7.890 (m, 2H), 8.101 (m, 1H) |
| 4-[(1S,3S)-3-(4-Amino-5-fluoro-2-oxo-2H-pyrimidin-1-yl)-cyclopentylsulfamoyl]-benzoic acid methyl ester | A | 410.42 (411.2) | L (1.960) | |
| N-[(1S,3S)-3-(4-Amino-5-fluoro-2-oxo-2H-pyrimidin-1-yl)-cyclopentyl]-3-((E)-styryl)-benzenesulfonamide | A | 454.52 (454.9) | L (2.602) | |
| tert-butyl (1S,3S)-3-(4-amino-5-fluoro-2-oxopyrimidin-1(2H)-yl)cyclopentyl(4-vinylphenylsulfonyl)carbamate | A | 478.54 (479.0) | L (2.731) | |
| methyl 3-(N-((1S,3S)-3-(4-amino-5-fluoro-2-oxopyrimidin-1(2H)-yl)cyclopentyl)-N-(tert-butoxycarbonyl)sulfamoyl)-benzoate | A | 510.54 (510.9) | L (4.195) | |
| N-[(1S,3S)-3-(4-Amino-5-fluoro-2-oxo-2H-pyrimidin-1-yl)-cyclopentyl]-3-((E)-3,3-dimethyl-but-1-enyl)-benzenesulfonamide | A | 434.53 (435.0) | L (2.691) | |
| N-[(1S,3S)-3-(4-Amino-5-fluoro-2-oxo-2H-pyrimidin-1-yl)-cyclopentyl]-4-((E)-styryl)-benzenesulfonamide | A | 454.52 (454.9) | L (2.613) | |

TABLE 8-continued

| Chemical Name | Synth. | Calc. Mol. Wt. (Obs. Mol. Wt.) | HPLC Method (Time) | $^1$H NMR |
|---|---|---|---|---|
| 3-[(1S,3S)-3-(4-Amino-5-fluoro-2-oxo-2H-pyrimidin-1-yl)-cyclopentylsulfamoyl]-benzoic acid methyl ester | A | 410.42 (411.0) | L (1.947) | |
| N-[(1S,3S)-3-(4-Amino-5-fluoro-2-oxo-2H-pyrimidin-1-yl)-cyclopentyl]-4-vinyl-benzenesulfonamide | A | 378.42 (378.9) | L (2.088) | |
| 4'-Methoxy-biphenyl-4-sulfonic acid [(1S,3S)-3-(4-amino-5-fluoro-2-oxo-2H-pyrimidin-1-yl)-cyclopentyl]-amide | A | 458.51 (459.0) | N (3.525) | |
| 2'-Fluoro-biphenyl-4-sulfonic acid [(1S,3S)-3-(4-amino-5-fluoro-2-oxo-2H-pyrimidin-1-yl)-cyclopentyl]-amide | A | 446.47 (447.1) | N (3.631) | |
| 4'-Methyl-biphenyl-3-sulfonic acid [(1S,3S)-3-(4-amino-5-fluoro-2-oxo-2H-pyrimidin-1-yl)-cyclopentyl]-amide | A | 442.51 (443.2) | O (1.950) | |
| 3'-Methoxy-biphenyl-3-sulfonic acid [(1S,3S)-3-(4-amino-5-fluoro-2-oxo-2H-pyrimidin-1-yl)-cyclopentyl]-amide | A | 458.51 (459.2) | O (1.850) | |
| N-[(1S,3S)-3-(4-Amino-5-fluoro-2-oxo-2H-pyrimidin-1-yl)-cyclopentyl]-3-bromo-benzenesulfonamide | A | 431.28 (432.9) | P (1.11) | |
| 4'-Methoxy-biphenyl-3-sulfonic acid [(1S,3S)-3-(4-amino-5-fluoro-2-oxo-2H-pyrimidin-1-yl)-cyclopentyl]-amide | A | 458.51 (459.2) | O (1.840) | (400 MHz, d$_6$-DMSO) δ: 8.00 (s, 1H), 7.86 (ad, J = 6.8 Hz, 2H), 7.71 (ad, J = 7.6H), 7.65-7.59 (m, 3H), 7.05 (d, J = 8.4 Hz, 2H), 4.73 (tt, J = 8.6, 8.6 Hz, 1H), 3.79 (as, 4H), 1.85 (m, 2H), 1.72 (at, J = 7.6 Hz, 2H), 1.55 (m, 1H), 1.37 (m, 1H) |
| N-[(1S,3S)-3-(4-Amino-5-fluoro-2-oxo-2H-pyrimidin-1-yl)-cyclopentyl]-3-naphthalen-2-yl-benzenesulfonamide | A | 478.54 (497.2) | Q (3.030) | |
| N-[(1S,3S)-3-(4-Amino-5-fluoro-2-oxo-2H-pyrimidin-1-yl)-cyclopentyl]-4-naphthalen-2-yl-benzenesulfonamide | A | 478.54 (479.2) | Q (3.020) | |
| N-[(1S,3S)-3-(4-Amino-5-fluoro-2-oxo-2H-pyrimidin-1-yl)-cyclopentyl]-4-naphthalen-1-yl-benzenesulfonamide | A | 478.54 (497.2) | Q (3.010) | |
| 4'-tert-Butyl-biphenyl-3-sulfonic acid [(1S,3S)-3-(4-amino-5-fluoro-2-oxo-2H-pyrimidin-1-yl)-cyclopentyl]-amide | A | 484.59 (485.0) | C (1.580) | |
| 4'-Trifluoromethyl-biphenyl-3-sulfonic acid [(1S,3S)-3-(4-amino-5-fluoro-2-oxo-2H-pyrimidin-1-yl)-cyclopentyl]-amide | A | 496.48 (497.0) | O (2.065) | |
| 3'-Trifluoromethyl-biphenyl-3-sulfonic acid [(1S,3S)-3-(4-amino-5-fluoro-2-oxo-2H-pyrimidin-1-yl)-cyclopentyl]-amide | A | 496.48 (496.9) | C (1.570) | |
| 2',4'-Dichloro-biphenyl-3-sulfonic acid [(1S,3S)-3-(4-amino-5-fluoro-2-oxo-2H-pyrimidin-1-yl)-cyclopentyl]-amide | A | 497.37 (498.8) | R (1.450) | |
| 2'-Chloro-biphenyl-3-sulfonic acid [(1S,3S)-3-(4-amino-5-fluoro-2-oxo-2H-pyrimidin-1-yl)-cyclopentyl]-amide | A | 462.93 (463.0) | C (1.480) | |

TABLE 8-continued

| Chemical Name | Synth. | Calc. Mol. Wt. (Obs. Mol. Wt.) | HPLC Method (Time) | ¹H NMR |
|---|---|---|---|---|
| 4'-Chloro-biphenyl-3-sulfonic acid [(1S,3S)-3-(4-amino-5-fluoro-2-oxo-2H-pyrimidin-1-yl)-cyclopentyl]-amide | A | 462.93 (462.9) | C (1.550) | (400 MHz, d$_6$-DMSO) δ: 8.00 (s, 1H), 7.88 (d, J = 7.8 Hz, 1H), 7.82 (m, 2H), 7.75 (d, J = 8.2, 1H), 7.69 (ad, J = 8.6 Hz, 2H), 7.63 (t, J = 7.8 Hz, 1H), 7.52 (ad, J = 8.6, 3H), 7.28 (abs, 1H), 4.73 (tt, J = 8.4, 8.4 Hz, 1H), 3.75 (m, 1H), 1.80 (m, 2H), 1.67 (at, J = 8.4 Hz, 2H), 1.51 (m, 1H), 1.31 (m 1H) |
| 4'-[(1S,3S)-3-(4-Amino-5-fluoro-2-oxo-2H-pyrimidin-1-yl)-cyclopentylsulfamoyl]-biphenyl-4-carboxylic acid | A | 472.49 (473.1) | B (1.075) | |
| 4-Nitro-benzoic acid (1S,3S)-3-(4-amino-5-fluoro-2-oxo-2H-pyrimidin-1-yl)-cyclopentyl ester | A | 362.31 (363.3) | C (1.300) | |
| (1S,3S)-3-(4-amino-5-fluoro-2-oxopyrimidin-1(2H)-yl)cyclopentyl benzoate | A | 317.32 (318.3) | D (1.950) | (400 MHz, CD$_3$OD) δ: 1.81-2.01 (m, 2H), 2.20-2.38 (m, 4H), 2.39-2.50 (m, 1H), 5.15 (ddd, J = 16.7, 8.5, 1.5 Hz, 1H), 5.52-5.58 (m, 1H), 7.50 (app t, J = 6.3 Hz, 2H), 7.61 (app t, J = 6.4 Hz, 1H), 7.92 (d, J = 6.7 Hz, 1H), 8.04 (app dd, J = 8.0, 5.0 Hz, 2H) |
| 4-amino-5-fluoro-1-((1S,3S)-3-(isoindolin-2-yl)cyclopentyl)pyrimidin-2(1H)-one | G | 314.36 (315.0) | F (1.645) | |
| N-[(S)-3-((S)-4-Amino-5-fluoro-2-oxo-2H-pyrimidin-1-yl)-cyclopentyl]-4-nitro-benzamide | B | 361.33 (362.0) | F (1.793) | |
| N-[(S)-3-((S)-4-Amino-5-fluoro-2-oxo-2H-pyrimidin-1-yl)-cyclopentyl]-4-(1H-pyrazol-4-yl)-benzenesulfonamide | B | 418.45 (419.0) | F (1.690) | |
| Biphenyl-4-carboxylic acid (S)-3-((S)-4-amino-5-fluoro-2-oxo-2H-pyrimidin-1-yl)-cyclopentyl ester | A | 393.41 (394.0) | E (2.147) | |
| N-[(S)-3-((S)-4-Amino-5-fluoro-2-oxo-2H-pyrimidin-1-yl)-cyclopentyl]-4-benzyl-benzenesulfonamide | F | 442.51 (443.0) | E (2.135) | (300 MHz, MeOD) δ: 1.34-1.60 (m, 2H), 1.66-1.73 (m, 2H), 1.86-1.98 (m, 2H) 3.69-3.78 (m, 1H), 4.70-4.80 (m, 1H), 7.05-7.19 (m, 5H), 7.29 (dd, J = 8.4 Hz, 2H), 7.62-7.69 (m, 3H) |
| N-[(S)-3-((S)-4-Amino-5-fluoro-2-oxo-2H-pyrimidin-1-yl)-cyclopentyl]-4-pyridin-2-yl-benzenesulfonamide | A | 429.47 (430.0) | E (1.165) | (400 MHz, CDCl$_3$) δ: 1.29-1.55 (m, 2H), 1.88-2.11 (m, 4H), 3.90-3.96 (m, 1H), 7.41-7.46 (m, 1H), 7.77 (d, J = 7.8 Hz, 1H), 7.94-8.01 (m, 4H), 8.17 (d, J = 8.7 Hz, 3H), 8.67 (d, J = 5.1 Hz, 3H) |
| Biphenyl-4-carboxylic acid [(S)-3-((S)-4-amino-5-fluoro-2-oxo-2H-pyrimidin-1-yl)-cyclopentyl]-methyl-amide | G, B | 406.45 (407.0) | E (1.872) | |
| (1S,3S)-3-(4-amino-5-fluoro-2-oxopyrimidin-1(2H)-yl)cyclopentyl biphenyl-4-ylcarbamate | J | 408.43 (409.1) | C (1.210) | (400 MHz, CD$_3$OD) δ: 1.26 (m, 1H), 1.73 (m, 1H), 1.84 (M, 1H), 2.0-2.3 (m, 3H), 4.47 (m, 1H), 5.15 (t, J = 10.0 Hz, 1H), 7.31 (t, J = 7.2 Hz, 1H), 7.42 (t, J = 7.6 Hz, 2H), 7.60 (m, 4H), 7.75 (d, J = 8.0 Hz, 2H), 8.20 (d, J = 6.8 Hz, 1H) |

TABLE 8-continued

| Chemical Name | Synth. | Calc. Mol. Wt. (Obs. Mol. Wt.) | HPLC Method (Time) | $^1$H NMR |
|---|---|---|---|---|
| 4'-Hydroxymethyl-biphenyl-4-sulfonic acid [(1S,3S)-3-(4-amino-5-fluoro-2-oxo-2H-pyrimidin-1-yl)-cyclopentyl]-amide | A | 458.51 (459.1) | K (1.452) | |
| 4'-[(1S,3S)-3-(4-Amino-5-fluoro-2-oxo-2H-pyrimidin-1-yl)-cyclopentylsulfamoyl]-biphenyl-4-carboxylic acid amide | A | 471.51 (472.1) | L (1.805) | |
| 4'-[(1S,3S)-3-(4-Amino-5-fluoro-2-oxo-2H-pyrimidin-1-yl)-cyclopentylsulfamoyl]-biphenyl-4-carboxylic acid methylamide | A | 485.53 (486.2) | L (1.882) | |
| 4'-[(1S,3S)-3-(4-Amino-5-fluoro-2-oxo-2H-pyrimidin-1-yl)-cyclopentylsulfamoyl]-biphenyl-3-carboxylic acid amide | A | 471.51 (472.1) | L (1.863) | |
| N-[(1S,3S)-3-(4-Amino-5-fluoro-2-oxo-2H-pyrimidin-1-yl)-cyclopentyl]-4-(1-methyl-1H-pyrazol-4-yl)-benzenesulfonamide | A | 432.47 (433.0) | L (1.812) | (400 MHz, CD$_3$OD) δ: 1.53 (m, 1H), 1.762 (m, 1H), 1.99 (q, J = 8.4 Hz, 2H), 2.053 (m, 1H), 2.137 (m, 1H), 3.886 (t, J = 6.8 Hz, 1H), 3.945 (s, 3H), 4.863 (m, J = 8.8 Hz, 1H), 7.74 (d, J = 8.8 Hz, 2H), 7.842 (d, J = 8.8 Hz, 2H), 7.924 (s, 1H), 8.100 (s, 1H), 8.242 (d, J = 6.4, 1H) |
| 4'-[(1S,3S)-3-(4-Amino-5-fluoro-2-oxo-2H-pyrimidin-1-yl)-cyclopentylsulfamoyl]-biphenyl-4-carboxylic acid dimethylamide | A | 499.56 (500.1) | L (1.972) | |
| 4-{4-[(1S,3S)-3-(4-Amino-5-fluoro-2-oxo-2H-pyrimidin-1-yl)-cyclopentylsulfamoyl]-phenyl}-3,6-dihydro-2H-pyridine-1-carboxylic acid tert-butyl ester | A | 533.62 (534.0) | L (2.538) | |
| N-[(1S,3S)-3-(4-Amino-5-fluoro-2-oxo-2H-pyrimidin-1-yl)-cyclopentyl]-4-(1,2,3,6-tetrahydro-pyridin-4-yl)-benzenesulfonamide | A | 433.50 (434.2) | L (1.392) | (400 MHz, CD$_3$OD) δ: 1.50 (m, 1H), 1.70 (m, 1H), 1.85 (t, J = 8 Hz, 2H), 2..05 (m, 2H), 2.73 (m, 2H), 3.76 (broad, 2H), 3.88 (m, J = 7 Hz, 1H), 4.62 (m, 2H), 4.78 (m, 1H), 6.33 (broad, 1H), 7.65 (d, J = 8 Hz, 2H), 7.747 (d, J = 6.8 Hz, 1H), 7.854 (d, J = 8.4 Hz, 2H) |
| N-[(1S,3S)-3-(4-Amino-5-fluoro-2-oxo-2H-pyrimidin-1-yl)-cyclopentyl]-4-piperidin-4-yl-benzenesulfonamide | E | 435.52 (436.2) | L (1.385) | (400 MHz, CD$_3$OD) δ: 1.52 (m, 1H), 1.71 (m, 1H), 1.84-2.0 (m, 4H), 2.00-2.16 (m, 4H), 3.0 (m, 1H), 3.11 (t, 2H), 3.49 (d, J = 12 Hz, 2H), 3.86 (m, 1H), 4.84 (m, 1H), 7.47 (d, J = 8 Hz, 1H), 7.75 (d, J = 6.4 Hz, 1H), 7.84 (d, J = 8.4 Hz, 1H) |
| 3'-[(1S,3S)-3-(4-Amino-5-fluoro-2-oxo-2H-pyrimidin-1-yl)-cyclopentylsulfamoyl]-biphenyl-4-carboxylic acid amide | A | 471.51 (472.1) | L (1.845) | |
| 3'-[(1S,3S)-3-(4-Amino-5-fluoro-2-oxo-2H-pyrimidin-1-yl)-cyclopentylsulfamoyl]-biphenyl-3-carboxylic acid amide | A | 471.51 (472.1) | L (1.890) | |

TABLE 8-continued

| Chemical Name | Synth. | Calc. Mol. Wt. (Obs. Mol. Wt.) | HPLC Method (Time) | ¹H NMR |
|---|---|---|---|---|
| N-[(1S,3S)-3-(4-Amino-5-fluoro-2-oxo-2H-pyrimidin-1-yl)-cyclopentyl]-4-(2,4-dioxo-1,2,3,4-tetrahydro-pyrimidin-5-yl)-benzenesulfonamide | A | 462.46 (463.2) | L (1.510) | (400 MHz, CD$_3$OD) δ: 1.48-1.52 (m, 1H), 1.66-1.74 (m, 1H), 1.89 (q, J = 7 Hz, 2H), 2.00-2.10 (m, 2H), 3.878 (m, J = 6 Hz, 1H), 4.61 (broad, 1H), 7.723 (s, 1H), 7.749 (s, 1H), 7.77 (d, 2H, J = 2 Hz), 7.853-7.875 (d, J = 9 Hz, 2H) |
| 4-Amino-1-((1R,3S,4S)-3-benzyloxy-4-hydroxy-cyclopentyl)-5-fluoro-1H-pyrimidin-2-one | L | 319.33 (320.1) | L (1.825) | |
| Biphenyl-4-sulfonic acid [(1R,2R,4R)-4-(4-amino-5-fluoro-2-oxo-2H-pyrimidin-1-yl)-2-hydroxy-cyclopentyl]-amide | L | 444.48 (445.1) | L (2.190) | |
| N-[(1R,2R,4R)-4-(4-Amino-5-fluoro-2-oxo-2H-pyrimidin-1-yl)-2-methoxy-cyclopentyl]-4-nitro-benzenesulfonamide | L | 427.41 (428.0) | M (3.335) | |
| N-((1S,3S)-3-(4-amino-5-fluoro-2-oxopyrimidin-1(2H)-yl)cyclopentyl)-4-(benzo[b]thiophen-2-yl)picolinamide | C | 449.51 (450.1) | S (3.005) | (400 MHz, d$_6$DMSO) δ: 8.89 (d, J = 7.8, 1H), 8.73 (d, J = 5.1, 1H), 8.31 (m, 2H), 8.08 (dd, J = 5.8, 3.3, 1H), 8.04 (d, J = 7.3, 1H), 7.99 (dd, J = 5.1, 2.0, 1H), 7.96 (dd, J = 5.94, 2.91, 1H), 7.56 (bs, 1H), 7.46 (m, 1H), 7.35 (bs, 1H), 5.02 (m, 1H), 4.64 (m, 1H), 2.10 (m, 4H), 1.75 (m 2H) |
| (S)-4-Amino-1-{(R)-3-[(biphenyl-4-ylmethyl)-amino]-cyclopentyl}-5-fluoro-1H-pyrimidin-2-one | G | 410.87 (411.0) | F (2.068) | (300 MHz, MeOD) δ: 1.69-1.78 (m, 1H), 2.93-3.03 (m, 1H), 5.40-5.50 (m, 1H), 5.99-6.01 (m, 1H), 6.27-6.29 (m, 1H), 7.43-7.52 (m, 4H), 7.60-7.72 (m, 4H), 7.85 (d, J = 6.6 Hz, 1H) |
| N-((1R,3S)-3-(4-amino-5-fluoro-2-oxopyrimidin-1(2H)-yl)cyclopentyl)biphenyl-4-sulfonamide | G | 428.48 (429.2) | C (2.310) | (400 MHz, CD$_3$OD) δ: 1.60-1.90 (m, 4H), 1.98 (m, 1H), 2.23 (m, 1H), 3.64 (dd, J = 6.8 Hz, 6.4 Hz, 1H), 4.69 (m, 1H), 4.84 (m, 1H), 7.39 (m, 1H), 7.44 (m, 2H), 7.65 (m, 2H), 7.81 (m, 2H), 7.94 (m, 2H) |
| 4-Amino-1-[(S)-1-(biphenyl-4-sulfonyl)-pyrrolidin-3-yl]-5-fluoro-1H-pyrimidin-2-one | H | 414.45 (415.1) | A (1.60) | |
| 4-Amino-1-[(S)-1-(biphenyl-4-sulfonyl)-pyrrolidin-3-yl]-1H-pyrimidin-2-one | H | 396.46 (397.1) | A (1.48) | (400 MHz, CD$_3$OD) δ: 2.08 (m, 2H), 3.39-3.46 (m, 1H), 3.51-3.63 (m, 3H), 5.26 (s, 1H), 6.06 (d, J = 6.0 Hz, 1H), 7.39-7.50 (m, 3H), 7.67 (m, 3H), 7.76 (d, J = 8.0 Hz, 2H), 7.84 (d, J = 8.0 Hz, 2H) |
| 4-Amino-1-[(S)-1-(4-bromo-benzenesulfonyl)-pyrrolidin-3-yl]-5-fluoro-1H-pyrimidin-2-one | H | 417.25 (419.0) | A (1.32) | |

TABLE 8-continued

| Chemical Name | Synth. | Calc. Mol. Wt. (Obs. Mol. Wt.) | HPLC Method (Time) | $^1$H NMR |
|---|---|---|---|---|
| 4-Amino-1-[(S)-1-(4-bromo-benzenesulfonyl)-pyrrolidin-3-yl]-1H-pyrimidin-2-one | H | 399.26 (401.0) | A (1.22) | |
| 4-Amino-1-[(S)-1-(biphenyl-4-carbonyl)-pyrrolidin-3-yl]-5-fluoro-1H-pyrimidin-2-one | I | 378.40 (379.0) | A (1.16) | |
| 4-Amino-1-[(R)-1-(biphenyl-4-sulfonyl)-pyrrolidin-3-yl]-5-fluoro-1H-pyrimidin-2-one | H | 414.45 (415.1) | A (1.63) | |
| 4-Amino-1-[(R)-1-(biphenyl-4-sulfonyl)-pyrrolidin-3-yl]-1H-pyrimidin-2-one | H | 396.46 (397.1) | A (2.86) | |
| 4-Nitro-benzoic acid (R)-4-((S)-4-amino-5-fluoro-2-oxo-2H-pyrimidin-1-yl)-cyclopent-2-enyl ester | A | 360.30 (361.1) | R (1.01) | |
| (S)-4-Amino-1-[(R)-4-(1,3-dihydro-isoindol-2-yl)-cyclopent-2-enyl]-5-fluoro-1H-pyrimidin-2-one | G | 312.34 (313.0) | F (1.703) | |
| 2-[(1R,4R)-4-(4-Amino-5-fluoro-2-oxo-2H-pyrimidin-1-yl)-cyclopent-2-enyl]-N-biphenyl-4-ylmethyl-acetamide | K | 418.46 (419.2) | C (1.400) | (400 MHz, CD$_3$OD) δ: 1.34 (m, 1H), 2.40 (m, 2H), 2.80 (M, 1H), 3.16 (br s, 1H), 4.40 (s, 2H), 5.60 (br s, 1H), 5.70 (m, 1H), 6.16 (m, 1H), 7.33 (m, 3H), 7.39 (m, 2H), 7.58 (m, 5H) |
| N-[(1S,4R)-4-(4-Amino-5-fluoro-2-oxo-2H-pyrimidin-1-yl)-cyclopent-2-enyl]-3-chloro-benzenesulfonamide | G | 384.81 (385.0) | C (1.290) | (400 MHz, CD$_3$OD) δ: 1.26 (m, 1H), 2.80 (m, 1H), 4.84 (M, 1H), 5.43 (m, 1H), 5.81 (m, 1H), 5.86 (m, 1H), 7.55 (m, 2H), 7.65 (m, 1H), 7.80 (m, 1H), 7.87 (m, 1H) |
| Biphenyl-4-sulfonic acid [(1S,4R)-4-(4-amino-5-fluoro-2-oxo-2H-pyrimidin-1-yl)-cyclopent-2-enyl]-amide | G | 426.47 (427.0) | H (1.620) | (400 MHz, CD$_3$OD) δ: 1.34 (m, 1H), 2.80 (M, 1H), 4.34 (br s, 1H), 5.42 (br s, 1H), 5.80 (br s, 1H), 5.89 (m, 1H), 7.38-7.60 (m, 4H), 7.67 (m, 2H), 7.80 (m, 2H), 7.95 (m, 2H) |

5.13. Cloning, Expression and Purification of Recombinant Deoxycytidine Kinase A full-length cDNA of deoxycytidine kinase was obtained by RT-PCR using known primers with human lymph node RNA (Clontech, Mountain View, Calif.) as template. This full length ORF was cloned into pCR4Blunt-Topo (Invitrogen, Carlsbad, Calif.). Protein expression and purification was adapted from the procedure described by Sabini et al., Nature Structure Biology 10, 513-519 (2003).

Here, the full length ORF of deoxycytidine kinase was subcloned into pET28(a+) (Novagen, San Diego, Calif.) using endonucleases (Nde1 and Xho1). The plasmid was transformed into a bacterial strain BL21 (DE3). A single colony was picked and grown in LB broth containing Kanamycin 50 μg/ml and 2% glucose. Cells were grown at 37° C. until OD$_{600}$ was 0.6. Then, 0.1 mM IPTG was added and the culture incubated at 30° C. for 16 hours. Cells were harvested by centrifugation and resuspended in 50 ml of 50 mM Tris, pH 8.0 containing 1 mg/ml of Lysozyme, 10% glycerol and 10 mM MgCl$_2$, 50 μg/ml of DNase 1 and 1 tablet of Roche protein inhibitor cocktail and incubated on ice for 30 minutes. Cells were then disrupted on ice using a homogenizer. Whole cell lysate were cleared by centrifugation at 20,000 rpm for 20 minutes. The supernatant was loaded onto a Ni-NTA Sepharose column (20 ml of bed volume) preequilibrated with 50 mM Tris, pH 8.0, containing 10 mM MgCl$_2$, 10% glycerol. The column was washed with the same buffer containing 20 mM imidazole until OD$_{280}$ reached the baseline at a flow rate of 2 ml/min. Deoxycytidine kinase was eluted with a gradient of 120 ml 0 to 800 mM imidazole in the same buffer. The protein peak was pooled and dialyzed against 2 liters of 50 mM Tris, pH 7.5 containing 5 mM MgCl$_2$, 1 mM EDTA, 5 mM DTT and 20% glycerol. Protein aliquots were stored at −80° C. Protein was at least 95% pure as estimated by the SDS-PAGE.

5.14. Deoxycytidine Kinase Filter Binding Assay

This filter binding assay is based on the binding of the deoxycytidine kinase reaction product dCMP to the positive charged DE-81 filter disk (Ives, D. H. and Wang S.-M., Methods Enzymol. 51:337-345 (1978)). Waterman DE-81 or Millipore DEAE 96 well plates were chosen as the binding media for the assay.

Deoxycytidine kinase at a concentration of 5 to 50 nM was incubated with 1 μM of $^3$H-labeled deoxycytidine (20 Ci/mmol) and 10 μM ATP in 50 μl of 50 mM Tris, pH 7.6, containing 5 mM MgCl$_2$, 0.5 mM DTT, 0.1% pluronic acid and 1 mg/ml BSA for 5 to 40 minutes at room temperature. Ten µl of 10 mM deoxycytidine was added and mixed. Ten to 20 µl of reaction solution (per well) was loaded to a DE-81 96 well plate pre-wetted with 1 mM ammonium formate, pH 3.6. The plate was washed three times with 1 mM ammonium formate, pH 3.6 and dried. The plate bottom was sealed with the plate seal and 100 µl of scintillation fluid was added per well and $^3$H-labeled products were counted by a TOPcount scintillation counter.

5.15. Deoxycytidine Kinase Cell-Based Assay

A simple and sensitive cell based assay was developed based on the known in vivo activation of cytosineb-D-arabinofuranoside (AraC) by deoxycytidine kinase: inhibition of deoxycytidine kinase would reverse the cytotoxicity of AraC.

A human T lymphoblastoid cell line CCRF-CEM (ATCC: CCL119) was seeded in 100 µl of a modified RPMI 1640 medium containing 30 nM AraC at 4,000 cells/well. Different concentration of deoxycytidine kinase inhibitors was added. The cells were grown at 37° C. for 3 days. Then, 100 µl of CellTiter-Glo Luminescent Cell Viability Assay reagent (Promega) was added and incubated at room temperature for 60 minutes. Chemiluminescence was recorded using a Tecan luminescence reader. The luminescence represents total ATP concentrations in the cells, which is proportional to cell number.

5.16. Thymidine and Uridine Kinase Inhibition Assays

Whole cell lysate made from CEM-CLL cells, as described above, were used as enzyme source.

Whole cell lysate were incubated with 1 µM of 3H-labeled thymidine (20 Ci/mmol) and 200 µM ATP in 50 µl of 50 mM Tris, pH 7.6, containing 5 mM MgCl$_2$, 0.5 mM DTT with or without compounds at various concentration for 5 to 40 min at room temperature. Then 10 µl of 10 mM cold thymidine was added and mixed. 10 to 20 µl of reaction solution (per well) was loaded to a DE-81 96 well plate pre-wetted with 1 mM ammonium formate, pH 3.6. The plate was washed three times with 1 mM ammonium formate, pH 3.6, and dried. The plate bottom was sealed with the plate seal and 100 µl of scintillation fluid was added per well, and $^3$H-labeled products were counted by a TOPcount scintillation counter.

For the uridine kinase inhibition assay, the procedure was the same except the ATP concentration was increased to 400 µM.

5.17. Calculating IC$_{50}$ Values

The IC$_{50}$ of a compound with regard to a given target is determined by fitting the relevant data, using the Levenburg Marquardt algorithm, to the equation:

$$y=A+((B-A)/(1+((C/x)^D)))$$

wherein A is the minimum y value; B is the maximum y value; C is the IC$_{50}$; and D is the slope. The calculation of the IC$_{50}$ is performed using XLFit4 software (ID Business Solutions Inc., Bridgewater, N.J. 08807) for Microsoft Excel (the above equation is model 205 of that software).

All publications cited above (e.g., patents and patent applications) are incorporated herein by reference in their entireties.

What is claimed is:

1. A compound of formula I:

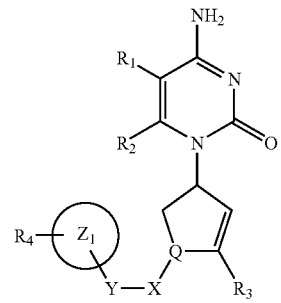

I or a pharmaceutically acceptable salt thereof, wherein:
Q is C or N;
X is a bond, NR$_5$, N(C(O)R$_5$), N(C(O)OR$_5$), O, S, SO$_2$, C, CH, or CH$_2$;
Y is a bond, C(O), C(O)NH, C(O)NH$_2$CH$_2$, SO$_2$, NR$_5$, N(C(O)R$_5$), N(C(O)OR$_5$), or CH$_2$, with the proviso that Y is not a bond if X is a bond;
or X and Y are taken together to provide one bond between Z$_1$ and Q;
Z$_1$ is optionally substituted cycloalkyl, aryl, or heterocycle;
R$_1$ is hydrogen, halogen, —OH, —NH$_2$, —NO$_2$, —CN, or optionally substituted alkyl;
R$_2$ is hydrogen, halogen, or optionally substituted alkyl;
R$_3$ is hydrogen, halogen, —OR$_6$ or —NR$_7$R$_8$;
R$_4$ is hydrogen, —C(O)(CH$_2$)$_n$R$_9$, —C(O)NH(CH$_2$)$_n$R$_9$, —NHC(O)(CH$_2$)$_n$R$_9$, or optionally substituted alkyl, aryl, heterocycle, alkyl-aryl, or alkyl-heterocycle;
R$_5$ is hydrogen or optionally substituted alkyl, aryl, heterocycle, alkyl-aryl or alkyl-heterocycle;
R$_6$ is hydrogen or optionally substituted alkyl, aryl, heterocycle, alkyl-aryl or alkyl-heterocycle;
R$_7$ and R$_8$ are each independently hydrogen, or optionally substituted alkyl, aryl, heterocycle, alkyl-aryl or alkyl-heterocycle, or taken together with the nitrogen atom to which they are attached, form an optionally substituted heterocycle;
R$_9$ is optionally substituted alkyl, aryl or heterocycle; and
n is 0-3.

2. The compound of claim 1, which is of formula II:

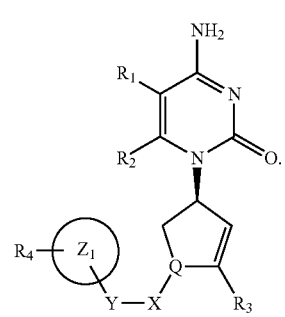

II

3. A compound of formula VIII:

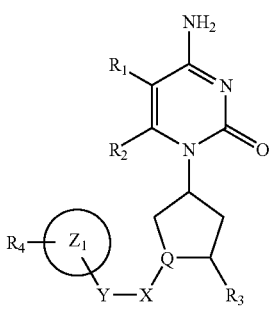

or a pharmaceutically acceptable salt thereof, wherein:

Q is C or N;

X is a bond, $NR_5$, $N(C(O)R_5)$, $N(C(O)OR_5)$, O, S, $SO_2$, C, CH, or $CH_2$;

Y is a bond, C(O), C(O)NH, $C(O)NH_2CH_2$, $SO_2$, $NR_5$, $N(C(O)R_5)$, $N(C(O)OR_5)$, or $CH_2$, with the proviso that Y is not a bond if X is a bond;

or X and Y are taken together to provide one bond between $Z_1$ and Q;

$Z_1$ is optionally substituted cycloalkyl, aryl, or heterocycle;

$R_1$ is hydrogen, halogen, —OH, —$NH_2$, —$NO_2$, —CN, or optionally substituted alkyl;

$R_2$ is hydrogen, halogen, or optionally substituted alkyl;

$R_3$ is hydrogen, halogen, —$OR_6$ or —$NR_7R_8$;

$R_4$ is hydrogen, —$C(O)(CH_2)_nR_9$, —$C(O)NH(CH_2)_nR_9$, —$NHC(O)(CH_2)_nR_9$, or optionally substituted alkyl, aryl, heterocycle, alkyl-aryl, or alkyl-heterocycle;

$R_5$ is hydrogen or optionally substituted alkyl, aryl, heterocycle, alkyl-aryl or alkyl-heterocycle;

$R_6$ is hydrogen or optionally substituted alkyl, aryl, heterocycle, alkyl-aryl or alkyl-heterocycle;

$R_7$ and $R_8$ are each independently hydrogen, or optionally substituted alkyl, aryl, heterocycle, alkyl-aryl or alkyl-heterocycle, or taken together with the nitrogen atom to which they are attached, form an optionally substituted heterocycle;

$R_9$ is optionally substituted alkyl, aryl or heterocycle; and n is 0-3;

with the proviso that $Z_1$ and $R_4$ taken together are not 4-methylphenyl when Q is N, X and Y taken together are $SO_2$, and $R_3$ is —$CH_2CH_2OH$.

4. The compound of claim 3, which is of formula IX:

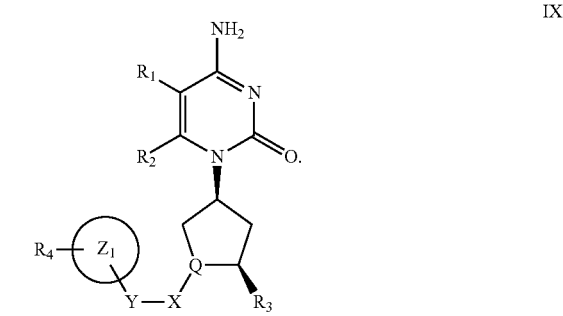

5. The compound of claim 3, wherein $Z_1$ is not substituted with anything other than $R_4$.

6. The compound of claim 3, wherein $Z_1$ is heteroaryl.

7. The compound of claim 6, wherein $Z_1$ is pyridine, pyridazine, pyrimidine, pyrazine, quinoline, quinoxaline, or quinazoline.

8. The compound of claim 3, wherein X is $NR_5$ and $R_5$ is hydrogen or methyl.

9. The compound of claim 3, wherein Y is $SO_2$ or C(O).

10. The compound of claim 3, wherein $R_1$ is hydrogen or halogen.

11. The compound of claim 3, wherein $R_2$ is hydrogen.

12. The compound of claim 3, wherein $R_3$ is hydrogen.

13. The compound of claim 3, wherein $R_4$ is an optionally substituted heteroaryl.

14. The compound of claim 3, wherein $R_4$ is an optionally substituted bicyclic heteroaryl.

15. The compound of claim 14, wherein $R_4$ is quinoline, quinoxaline, quinazoline, 1,7-naphthyridine, benzofuran, benzo[b]thiophene, thieno[2,3-b]pyridine, thieno[2,3-c]pyridine, indole, isoindole, or pyrrolo[3,4-c]pyridine.

16. A pharmaceutical dosage form comprising a compound of claim 1 or 3.

17. The dosage form of claim 16, which further comprises an excipient or diluent.

* * * * *